United States Patent
Reich et al.

(10) Patent No.: US 7,674,895 B2
(45) Date of Patent: Mar. 9, 2010

(54) COMPOSITIONS AND METHODS FOR SIRNA INHIBITION OF ANGIOGENESIS

(75) Inventors: Samuel Jotham Reich, Merion Station, PA (US); Michael J. Tolentino, Lakeland, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 680 days.

(21) Appl. No.: 11/518,524

(22) Filed: Sep. 8, 2006

(65) Prior Publication Data

US 2007/0149471 A1 Jun. 28, 2007

Related U.S. Application Data

(63) Continuation-in-part of application No. 10/294,228, filed on Nov. 14, 2002, now Pat. No. 7,148,342.

(60) Provisional application No. 60/398,417, filed on Jul. 24, 2002.

(51) Int. Cl.
C07H 21/04 (2006.01)
A01N 43/04 (2006.01)
A61K 31/70 (2006.01)

(52) U.S. Cl. ........................ 536/24.5; 514/44
(58) Field of Classification Search ................ 536/23.1, 536/24.3, 24.33, 24.5; 514/44
See application file for complete search history.

(56) References Cited

U.S. PATENT DOCUMENTS

| | | | |
|---|---|---|---|
| 5,639,736 A * | 6/1997 | Robinson | 514/44 |
| 6,037,329 A * | 3/2000 | Baird et al. | 514/44 |
| 6,177,401 B1 | 1/2001 | Ullrich et al. | |
| 6,506,559 B1 | 1/2003 | Fire et al. | |
| 2002/0086356 A1 | 7/2002 | Tuschl et al. | |
| 2002/0132788 A1 | 9/2002 | Lewis et al. | |
| 2002/0162126 A1 | 10/2002 | Beach et al. | |
| 2002/0173478 A1 | 11/2002 | Gewirtz | |
| 2003/0138407 A1 | 7/2003 | Lu et al. | |
| 2003/0153519 A1 | 8/2003 | Kay et al. | |
| 2003/0216335 A1 | 11/2003 | Lockridge et al. | |
| 2005/0019927 A1 | 1/2005 | Hildinger et al. | |
| 2006/0286073 A1 | 12/2006 | Tolentino et al. | |

(Continued)

FOREIGN PATENT DOCUMENTS

CA 2359180 A1 8/2000

(Continued)

OTHER PUBLICATIONS

Methods. Feb. 2000;26(2):199-213. Analysis of gene function in somatic mammalian cells using small interfering RNAs. Elbashir SM, Harborth J, Weber K, Tuschl T.*

(Continued)

*Primary Examiner*—Sean McGarry
*Assistant Examiner*—Terra Cotta Gibbs
(74) *Attorney, Agent, or Firm*—Pepper Hamilton LLP

(57) ABSTRACT

RNA interference using small interfering RNAs which are specific for the vascular endothelial growth factor (VEGF) gene and the VEGF receptor genes Flt-1 and Flk-1/KDR inhibit expression of these genes. Diseases which involve angiogenesis stimulated by overexpression of VEGF, such as diabetic retinopathy, age related macular degeneration and many types of cancer, can be treated by administering the small interfering RNAs.

18 Claims, 10 Drawing Sheets

U.S. PATENT DOCUMENTS

| | | |
|---|---|---|
| 2006/0292120 A1 | 12/2006 | Tolentino et al. |
| 2007/0003523 A1 | 1/2007 | Tolentino et al. |
| 2007/0037760 A1 | 2/2007 | Tolentino et al. |
| 2007/0037761 A1 | 2/2007 | Tolentino et al. |
| 2007/0037762 A1 | 2/2007 | Tolentino et al. |

FOREIGN PATENT DOCUMENTS

| | | |
|---|---|---|
| EP | 1144623 B1 | 8/2002 |
| WO | WO 95/04142 | 2/1995 |
| WO | WO 00/08141 | 2/2000 |
| WO | WO 01/68836 | 9/2001 |
| WO | WO 01/75164 | 10/2001 |
| WO | WO 02/44321 | 6/2002 |
| WO | WO 02/096927 A2 | 12/2002 |
| WO | WO 02/096957 A1 | 12/2002 |
| WO | WO 03/070910 A2 | 8/2003 |
| WO | WO 03/087367 A2 | 10/2003 |
| WO | WO 03/0087368 A2 | 10/2003 |
| WO | WO 03/099298 | 12/2003 |
| WO | WO 2004/013310 A2 | 2/2004 |
| WO | WO 2006/110813 A2 | 10/2006 |

OTHER PUBLICATIONS

Shi et al., Inhibition of renal cell carcinoma angiogenesis and growth by antisense oligonucleotides targeting vascular endothelial growth factor, 2002, British Journal of Cancer 87:119-126.

Rubinson et al., A lentivirus-based system to functionally silence genes in primary mammalian cells, stem cells and transgenic mice by RNA interference, Nat. Genetics, published online Feb. 18, 2003, doi: 10.1038/ng1117, vol. 33(3):401-446 (Abstract).

Shu et al., Sphingosine Kinase Mediates Vascular Endothelial Growth Factor-Induced Activation of Ras and Mitogen-Activated Protein Kinases, Nov. 2002, Mol. Cell Biol. 22(22):7758-7768.

Tuschl, 2002, The siRNA User Guide, rev. Oct. 11, 2002 http://www.mplbpc.gwdg.de/abteilungen/100/105/sirna.html.

Van Brunt, Signals Magazine, Shoot the Messenger, http:www.signalsmag.com/signalsmag..../3DF5AEF6049C88256C1D0055BAA, Aug. 22, 2002.

Holash et al., VEGF-Trap: A VEGF blocker with potent antitumor effects, 2002, PNAS USA 99(17):11393-11398.

Kim et al., Potent VEGF blockade causes regression of coopted vessels in a model of neuroblastoma, 2002, PNAS USA 99(17)11399-11404.

Novina et al., siRNA-directed inhibition of HIV-1 infection, 2002, Nat. Med. 8(7):681-686.

Xia et al., siRNA-mediated gene silencing in vitro and in vivo, 2002, Nat. Biotech. 20:1006-1010.

Elbashir et al., RNA interference is mediated by 21-and 22-nucleotide RNAs, 2001, Genes Dev. 15:188-200.

Elbashir et al., Duplexes of 21-nucleotide RNAs mediate RNA interference in cultured mammalian cells, 2001, Nature 411:494-498.

Fire et al., Potent and specific genetic interference by double-stranded RNA in *Caenorhabditis elegans*, 1998, Nature 391:806-811.

Bennett et al., Humoral response after administration of E1-deleted adenoviruses: immune privilege of the subretinal space, 1995, Hum. Gene Ther. 7(14):1763-1769 (Abstract).

Tischer et al., The human gene for vascular endothelial growth factor. Multiple protein forms are encoded through alternative exon splicing, Jun. 25, 1991, J. Biol. Chem. 266(18):11947-11954 (Abstract).

Erickson, RNAi Revs Up, Oct. 2002, Start-Up, RNAi Revs Up (A#2002900168) pp. 1-12.

Houck et al., The Vascular Endothelial Growth Factor Family: Identification of a Fourth Molecular Species and Characterization of Alternative Splicing of RNA, 1991, Molecular Endoc. 5(12)1806-1814.

Brantl, Antisense-RNA regulation and RNA Interference, 2002, Biochimica et Biophysics Acta 1575:15-25.

Reich et al., Small interfering RNA (siRNA) targeting *VEGF* effectively inhibits ocular neovascularization in a mouse model, 2003, Molecular Vision 9(31):210-216.

Marchand et al. "Blockade of in vivo VEGF-mediated angiogenesis by antisense gene therapy: role of Flk-1 and Flt-1 receptors" 2002, Am. J. Physiol. Heart Circ. Physiol. 282:194-204.

\* cited by examiner

SEQUENCE LISTING

<160> NUMBER OF SEQ ID NOS: 85

<210> SEQ ID NO 1
<211> LENGTH: 2250
<212> TYPE: DNA
<213> ORGANISM: Mus musculus

<400> SEQUENCE: 1

```
tgagccaggc tggcaggaag gagcctccct cagggtttcg ggaaccagac ctctcaccgg      60
aaagaccgat taaccatgtc accaccacgc catcatcgtc accgttgaca gaacagtcct     120
taatccagaa agcctgacat gaaggaagag gagactcttc gaggagcact ttgggtccgg     180
agggcgagac tccggcagac gcattccgg gcaggtgacc aagcacggtc cctcgtggga     240
ctggattcgc cattttctta tatctgctgc taaatcgcca agcccggaag attagggttg     300
tttctgggat tcctgtagac acaccccacc acatacacac atatatatat attatatata     360
taaataaata tatatgtttt atatataaaa tatatatata ttctttttttt taaattaact     420 ctgctaatgt tattggtgtc ttcactggat atgtttgact gctgtggact tgtgttggga     480
ggaggatgtc ctcactcgga tgccgacatg ggagacaatg ggatgaaagg cttcagtgtg     540
gtctgagaga ggccgaagtc cttttgcctg ccggggagca agcaaggcca gggcacgggg     600
```

-continued

| | |
|---|---:|
| gcacattggc tcacttccag aaacacgaca aacccattcc tggccctgag tcaagaggac | 660 |
| agagagacag atgatgacac agaaagagat aaagatgccg gttccaacca gaagtttggg | 720 |
| gagcctcagg acatggcatg ctttgtggat ccccatgata gtctacaaaa gcaccccgcc | 780 |
| cctctgggca ctgcctggaa gaatcgggag cctggccagc cttcagctcg ctcctccact | 840 |
| tctgaggggc ctaggaggcc tcccacaggt gtcccggcaa gagaagacac ggtggtggaa | 900 |
| gaagaggcct ggtaatggcc cctcctcctg ggacccctct gtcctctcct tacccccacct | 960 |
| cctgggtaca gcccaggagg accttgtgtg atcagaccat tgaaaccact aattctgtcc | 1020 |
| ccaggagact tggctctgtg tgtgagtggc ttacccttcc tcatcttccc ttcccaaggc | 1080 |
| acagagcaat ggggcaggac ccgcaagccc ctcacggagg cagagaaaag agaaagtgtt | 1140 |
| ttatatacgg tacttattta atagccctt ttaattagaa attaaaacag ttaatttaat | 1200 |
| taaagagtag ggttttttc agtattcttg gttaatattt aatttcaact atttatgaga | 1260 |
| tgtatctctc gctctctctt atttgtactt atgtgtgtgt gtgtgtgtgt gtgtgtgtgt | 1320 |
| gtgtgtgtgt gtatgaaatc tgtgtttcca atctctctct cccagatcgg tgacagtcac | 1380 |
| tagcttgtcc tgagaagata tttaattttg ctaacactca gctctgccct cccttgtccc | 1440 |
| caccacacat tcctttgaaa taaggtttca atatacattt acatactata tatatatttg | 1500 |
| gcaacttgtg tttgtatata aatatatata tatatatatg tttatgtata tatgtgattc | 1560 |
| tgataaaata gacattgcta ttctgttttt tatatgtaaa aacaaaacaa gaaaaataga | 1620 |
| gaattctaca tactaaatct ctctccttttt ttaattttaa tatttgttat catttattta | 1680 |
| ttggtgctac tgtttatccg taataattgt gggggaaaaa gatattaaca tcacgtcttt | 1740 |
| gtctctagag cagttttccg agatattccg tagtacatat ttattttaa acagcaacaa | 1800 |
| agaaatacag atatatctta aaaaaaaagc attttgtatt aaagaattga attctgatct | 1860 |
| caaagctctc cctggtctct ccttctctcc tgggccctcc tgtctcgctt tccctcctcc | 1920 |
| tttgggtac atagtttttg tcttaggttt gagaagcagt ccctggagta gaatatgggg | 1980 |
| tgacccatcc attcctgggc ggaggggaga tggctccttt gccaagggtc ctcacactac | 2040 |
| gtggtactct gttccttgtc agacaaggat ggggcatgt ctccaggtgc taactggaga | 2100 |
| tcggagagag ctgttggctg cagctggcca ggatttgggc atgccgggga catgggaggc | 2160 |
| tgtgagccca gcatgcagtt tacttctggg tgctaaatgg aagagtccag taaaaagagt | 2220 |
| cttgcccatg ggattccatt ccgctttgtg | 2250 |

<210> SEQ ID NO 2
<211> LENGTH: 444
<212> TYPE: DNA
<213> ORGANISM: Homo sapiens

<400> SEQUENCE: 2

| | |
|---|---:|
| atgaactttc tgctgtcttg ggtgcattgg agccttgcct tgctgctcta cctccaccat | 60 |
| gccaagtggt cccaggctgc acccatggca gaaggaggag ggcagaatca tcacgaagtg | 120 |
| gtgaagttca tggatgtcta tcagcgcagc tactgccatc caatcgagac cctggtggac | 180 |
| atcttccagg agtaccctga tgagatcgag tacatcttca agccatcctg tgtgccctg | 240 |
| atgcgatgcg ggggctgctg caatgacgag ggcctggagt gtgtgcccac tgaggagtcc | 300 |
| aacatcacca tgcagattat gcggatcaaa cctcaccaag gccagcacat aggagagatg | 360 |
| agcttcctac agcacaacaa atgtgaatgc agaccaaaga agatagagc aagacaagaa | 420 |
| aaatgtgaca agccgaggcg gtga | 444 |

<210> SEQ ID NO 3
<211> LENGTH: 576
<212> TYPE: DNA
<213> ORGANISM: Homo sapiens

<400> SEQUENCE: 3

| | | | | | |
|---|---|---|---|---|---|
| atgaactttc | tgctgtcttg | ggtgcattgg | agccttgcct | tgctgctcta | cctccaccat | 60 |
| gccaagtggt | cccaggctgc | acccatggca | gaaggaggag | ggcagaatca | tcacgaagtg | 120 |
| gtgaagttca | tggatgtcta | tcagcgcagc | tactgccatc | caatcgagac | cctggtggac | 180 |
| atcttccagg | agtaccctga | tgagatcgag | tacatcttca | agccatcctg | tgtgccsctg | 240 |
| atgcgatgcg | ggggctgctg | caatgacgag | ggcctggagt | gtgtgcccac | tgaggagtcc | 300 |
| aacatcacca | tgcagattat | gcggatcaaa | cctcaccaag | gccagcacat | aggagagatg | 360 |
| agcttcctac | agcacaacaa | atgtgaatgc | agaccaaaga | aagatagagc | aagacaagaa | 420 |
| aatccctgtg | gccttgctc | agagcggaga | aagcatttgt | ttgtacaaga | tccgcagacg | 480 |
| tgtaaatgtt | cctgcaaaaa | cacagactcg | cgttgcaagg | cgaggcagct | tgagttaaac | 540 |
| gaacgtactt | gcagatgtga | caagccgagg | cggtga | | | 576 |

<210> SEQ ID NO 4
<211> LENGTH: 648
<212> TYPE: DNA
<213> ORGANISM: Homo sapiens

<400> SEQUENCE: 4

| | | | | | |
|---|---|---|---|---|---|
| atgaactttc | tgctgtcttg | ggtgcattgg | agccttgcct | tgctgctcta | cctccaccat | 60 |
| gccaagtggt | cccaggctgc | acccatggca | gaaggaggag | ggcagaatca | tcacgaagtg | 120 |
| gtgaagttca | tggatgtcta | tcagcgcagc | tactgccatc | caatcgagac | cctggtggac | 180 |
| atcttccagg | agtaccctga | tgagatcgag | tacatcttca | agccatcctg | tgtgccsctg | 240 |
| atgcgatgcg | ggggctgctg | caatgacgag | ggcctggagt | gtgtgcccac | tgaggagtcc | 300 |
| aacatcacca | tgcagattat | gcggatcaaa | cctcaccaag | gccagcacat | aggagagatg | 360 |
| agcttcctac | agcacaacaa | atgtgaatgc | agaccaaaga | aagatagagc | aagacaagaa | 420 |
| aaaaaatcag | ttcgaggaaa | gggaaagggg | caaaaacgaa | agcgcaagaa | atcccggtat | 480 |
| aagtcctgga | gcgttccctg | tgggccttgc | tcagagcgga | gaaagcattt | gtttgtacaa | 540 |
| gatccgcaga | cgtgtaaatg | ttcctgcaaa | aacacagact | cgcgttgcaa | ggcgaggcag | 600 |
| cttgagttaa | acgaacgtac | ttgcagatgt | gacaagccga | ggcggtga | | 648 |

<210> SEQ ID NO 5
<211> LENGTH: 670
<212> TYPE: DNA
<213> ORGANISM: Homo sapiens

<400> SEQUENCE: 5

| | | | | | |
|---|---|---|---|---|---|
| gccttgctgc | tctacctcca | ccatgccaag | tggtcccagg | ctgcacccat | ggcagaagga | 60 |
| ggagggcaga | atcatcacga | agtggtgaag | ttcatggatg | tctatcagcg | cagctactgc | 120 |
| catccaatcg | agaccctggt | ggacatcttc | caggagtacc | ctgatgagat | cgagtacatc | 180 |
| ttcaagccat | cctgtgtgcc | cctgatgcga | tgcgggggct | gctgcaatga | cgagggcctg | 240 |
| gagtgtgtgc | ccactgagga | gtccaacatc | accatgcaga | ttatgcggat | caaacctcac | 300 |
| caaggccagc | acataggaga | gatgagcttc | ctacagcaca | acaaatgtga | atgcagacca | 360 |
| aagaaggata | gagcaagaca | agaaaaaaaa | tcagttcgag | gaaagggaaa | ggggcaaaaa | 420 |

```
cgaaagcgca agaaatcccg gtataagtcc tggagcgttt acgttggtgc ccgctgctgt    480
ctaatgccct ggagcctccc tggcccccat ccctgtgggc cttgctcaga gcggagaaag    540
catttgtttg tacaagatcc gcagacgtgt aaatgttcct gcaaaaacac agactcgcgt    600
tgcaaggcga ggcagcttga gttaaacgaa cgtacttgca gatgtgacaa gccgaggcgg    660
tgatgaatga                                                           670
```

<210> SEQ ID NO 6
<211> LENGTH: 1137
<212> TYPE: DNA
<213> ORGANISM: Homo sapiens

<400> SEQUENCE: 6

```
atgctcattg tccagactgg ggtcagatca gcaaacaaag ggcctctgat ggtgattgtt     60
gaatattgca aatatggaaa tctatccaac tacctcaaga gcaaatatga cttattttt     120 ctcgacaagg atgtggcatc acacatggag cgtaagaaag aaaaaatgga gccaggcctg    180
gaacaaggca agaaaccaaa actagatagc atcaccagca gcgagagctt gggagctcc    240 aagtttcagg aagataaaaa tctgagtgat gttgaggaag aggaggattc tgatggtttc    300
taccaggagc ccatcactat ggaagatctg atttcttaca gttttcaagt ggccagaggc    360
atgaagtttc tgtcttccag aaagtgcatt cattgggacc tggcagcaag aaacattctt    420
ttatctgaga acaatgtggt gaagatttgt gattttggcc ttgcccagga tatttacaag    480
aacgccgatt atgtgagaaa aggaggtggg tctccatacc caggagtgca aatggatgag    540
cacttctgca gttgcctgag ggaaggcatg aggatgagag ctgctgagta ctccactcct    600
gaaatctatc agatcatgct ggactgcagg cacaaagacc caaagaaag gccaagattt    660 gcagaacttg tggaaaaact agaaaatagt gggtttacat actcaactcc tgccttctct    720
gaggacttct tcaaggaagg tatttcagct cccaagttta gttcaggaag ctctgatgat    780
gtcagatacg taaatgcttt caagttcatg agcctggaaa gaatcaaaac cttttgaagaa    840 cttttgccaa atgccacctc catgtttgat gactaccagg gggacagcag cgctctgctg    900
gcctctccca tgctgaagcg cttcaccagg actgacagca aacccaaggc ctcgctcaag    960
attgacttga gactaactag caaaagtaag aagtcggggc tttctgatgt cagcaggccc    1020
agtttctgcc attccaacag tgggcacatc agcaaaggca agggcaggtt cacctacgac    1080
aacgccgagc tggaaaggaa gacggcgtgc tgctccccgc ccctctggga gttgtag      1137
```

<210> SEQ ID NO 7
<211> LENGTH: 5830
<212> TYPE: DNA
<213> ORGANISM: Homo sapiens

<400> SEQUENCE: 7

```
actgagtccc gggaccccgg gagagcggtc agtgtgtggt cgctgcgttt cctctgcctg     60
cgccgggcat cacttgcgcg ccgcagaaag tccgtctggc agcctggata tcctctccta    120
ccggcacccg cagacgcccc tgcagccgcc ggtcggcgcc cgggctccct agccctgtgc    180
gctcaactgt cctgcgctgc ggggtgccgc gagttccacc tccgcgcctc cttctctaga    240
caggcgctgg gagaaagaac cggctcccga gttctgggca tttcgcccgg ctcgaggtgc    300
aggatgcaga gcaaggtgct gctgccgtc gcctgtggc tctgcgtgga cccgggcc     360 gcctctgtgg ggttgcctag tgtttctctt gatctgccca ggctcagcat acaaaaagac    420
atacttacaa ttaaggctaa tacaactctt caaattactt gcagggaaca gagggacttg    480
```

-continued

```
gactggcttt ggcccaataa tcagagtggc agtgagcaaa gggtggaggt gactgagtgc      540
agcgatggcc tcttctgtaa gacactcaca attccaaaag tgatcggaaa tgacactgga      600
gcctacaagt gcttctaccg ggaaactgac ttggcctcgg tcatttatgt ctatgttcaa      660
gattacagat ctccatttat tgcttctgtt agtgaccaac atggagtcgt gtacattact      720
gagaacaaaa acaaaactgt ggtgattcca tgtctcgggt ccatttcaaa tctcaacgtg      780
tcactttgtg caagataccc agaaaagaga tttgttcctg atggtaacag aatttcctgg      840
gacagcaaga agggctttac tattcccagc tacatgatca gctatgctgg catggtcttc      900
tgtgaagcaa aaattaatga tgaaagttac cagtctatta tgtacatagt tgtcgttgta      960
gggtatagga tttatgatgt ggttctgagt ccgtctcatg gaattgaact atctgttgga     1020
gaaaagcttg tcttaaattg tacagcaaga actgaactaa atgtggggat tgacttcaac     1080
tgggaatacc cttcttcgaa gcatcagcat aagaaacttg taaaccgaga cctaaaaacc     1140
cagtctggga gtgagatgaa gaaatttttg agcaccttaa ctatagatgg tgtaacccgg     1200
agtgaccaag gattgtacac ctgtgcagca tccagtgggc tgatgaccaa gaagaacagc     1260
acatttgtca gggtccatga aaaacctttt gttgcttttg gaagtggcat ggaatctctg     1320
gtggaagcca cggtggggga gcgtgtcaga atccctgcga agtaccttgg ttacccaccc     1380
ccagaaataa aatggtataa aaatggaata ccccttgagt ccaatcacac aattaaagcg     1440
gggcatgtac tgacgattat ggaagtgagt gaaagagaca caggaaatta cactgtcatc     1500
cttaccaatc ccatttcaaa ggagaagcag agccatgtgg tctctctggt tgtgtatgtc     1560
ccaccccaga ttggtgagaa atctctaatc tctcctgtgg attcctacca gtacggcacc     1620
actcaaacgc tgcatgtgta cggtctatgcc attcctcccc gcatcacat ccactggtat      1680 tggcagttgg aggaagagtg cgccaacgag cccagccaag ctgtctcagt gacaaaccca     1740 taccettgtg aagaatggag aagtgtggag gacttccagg gaggaaataa aattgaagtt     1800
aataaaaatc aatttgctct aattgaagga aaaaacaaaa ctgtaagtac ccttgttatc     1860
caagcggcaa atgtgtcagc tttgtacaaa tgtgaagcgg tcaacaaagt cgggagagga     1920
gagagggtga tctccttcca cgtgaccagg ggtcctgaaa ttactttgca acctgacatg     1980
cagcccactg agcaggagag cgtgtctttg tggtgcactg cagacagatc tacgtttgag     2040
aacctcacat ggtacaagct tggcccacag cctctgccaa tccatgtggg agagttgccc     2100
acacctgttt gcaagaactt ggatactctt tggaaattga atgccaccat gttctctaat     2160
agcacaaatg acattttgat catggagctt aagaatgcat ccttgcagga ccaaggagac     2220
tatgtctgcc ttgctcaaga caggaagacc aagaaaagac attgcgtggt caggcagctc     2280
acagtcctag agcgtgtggc acccacgatc acaggaaacc tggagaatca gacgacaagt     2340 attgggaaa gcatcgaagt ctcatgcacg gcatctggga atcccctcc acagatcatg      2400 tggtttaaag ataatgagac ccttgtagaa gactcaggca ttgtattgaa ggatgggaac     2460
cggaacctca ctatccgcag agtgaggaag gaggacgaag gcctctacac ctgccaggca     2520
tgcagtgttc ttggctgtgc aaaagtggag gcattttca taatagaagg tgcccaggaa      2580
aagacgaact tggaaatcat tattctagta ggcacggcgg tgattgccat gttcttctgg     2640
ctacttcttg tcatcatcct acggaccgtt aagcgggcca atgagggga actgaagaca      2700 ggctacttgt ccatcgtcat ggatccagat gaactcccat tggatgaaca ttgtgaacga     2760
ctgccttatg atgccagcaa atgggaattc cccagagacc ggctgaagct aggtaagcct     2820
cttggccgtg gtgcctttgg ccaagtgatt gaagcagatg cctttggaat tgacaagaca     2880
```

```
gcaacttgca ggacagtagc agtcaaaatg ttgaaagaag gagcaacaca cagtgagcat    2940
cgagctctca tgtctgaact caagatcctc attcatattg gtcaccatct caatgtggtc    3000
aaccttctag gtgcctgtac caagccagga gggccactca tggtgattgt ggaattctgc    3060
aaatttggaa acctgtccac ttacctgagg agcaagagaa atgaatttgt cccctacaag    3120
accaaagggg cacgattccg tcaagggaaa gactacgttg gagcaatccc tgtggatctg    3180
aaacggcgct tggacagcat caccagtagc cagagctcag ccagctctgg atttgtggag    3240
gagaagtccc tcagtgatgt agaagaagag gaagctcctg aagatctgta taaggacttc    3300
ctgaccttgg agcatctcat ctgttacagc ttccaagtgg ctaagggcat ggagttcttg    3360
gcatcgcgaa agtgtatcca cagggacctg gcggcacgaa atatcctctt atcggagaag    3420
aacgtggtta aaatctgtga ctttggcttg cccgggata tttataaaga tccagattat    3480
gtcagaaaag gagatgctcg cctccctttg aaatggatgg ccccagaaac aattttgac     3540 agagtgtaca caatccagag tgacgtctgg tcttttggtg ttttgctgtg ggaaatattt    3600
tccttaggtg cttctcccata tcctggggta agattgatg aagaattttg taggcgattg    3660
aaagaaggaa ctagaatgag ggcccctgat tatactacac cagaaatgta ccagaccatg    3720
ctggactgct ggcacgggga gcccagtcag agacccacgt tttcagagtt ggtggaacat    3780
tgggaaaatc tcttgcaagc taatgctcag caggatggca aagactacat tgttcttccg    3840
atatcagaga ctttgagcat ggaagaggat tctggactct ctctgcctac ctcacctgtt    3900
tcctgtatgg aggaggagga agtatgtgac cccaaattcc attatgacaa cacagcagga    3960
atcagtcagt atctgcagaa cagtaagcga aagagccggc ctgtgagtgt aaaaacatt    4020 gaagatatcc cgttagaaga accagaagta aaagtaatcc cagatgacaa ccagacggac    4080
agtggtatgg ttcttgcctc agaagagctg aaaactttgg aagacagaac caaattatct    4140
ccatcttttg gtggaatggt gcccagcaaa agcaggagt ctgtggcatc tgaaggctca     4200
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt ttaaaaggaa    4380
gcatccacac cccaactccc ggacatcaca tgagaggtct gctcagattt tgaagtgttg    4440
ttctttccac cagcaggaag tagccgcatt tgattttcat ttcgacaaca gaaaaaggac    4500
ctcggactgc agggagccag tcttctaggc atatcctgga agaggcttgt gacccaagaa    4560
tgtgtctgtg tcttctccca gtgttgacct gatcctcttt tttcattcat ttaaaaagca    4620
ttatcatgcc cctgctgcgg gtctcaccat gggtttagaa caaagagctt caagcaatgg    4680
ccccatcctc aaagaagtag cagtacctgg ggagctgaca cttctgtaaa actagaagat    4740
aaaccaggca acgtaagtgt tcgaggtgtt gaagatggga aggatttgca gggctgagtc    4800
tatccaagag gctttgttta ggacgtgggt cccaagccaa gccttaagtg tggaattcgg    4860
attgatagaa aggaagacta acgttacctt gctttggaga gtactggagc ctgcaaatgc    4920
attgtgtttg ctctggtgga ggtgggcatg gggtctgttc tgaaatgtaa agggttcaga    4980
cggggtttct ggttttagaa ggttgcgtgt tcttcgagtt gggctaaagt agagttcgtt    5040
gtgctgtttc tgactcctaa tgagagttcc ttccagaccg ttagctgtct ccttgccaag    5100
ccccaggaag aaaatgatgc agctctggct ccttgtctcc caggctgatc ctttattcag    5160
aataccacaa agaaaggaca ttcagctcaa ggctccctgc cgtgttgaag agttctgact    5220
gcacaaacca gcttctggtt tcttctggaa tgaataccct catatctgtc ctgatgtgat    5280
```

-continued

| | |
|---|---|
| atgtctgaga ctgaatgcgg gaggttcaat gtgaagctgt gtgtggtgtc aaagtttcag | 5340 |
| gaaggatttt acccttttgt tcttccccct gtccccaacc cactctcacc ccgcaaccca | 5400 |
| tcagtatttt agttatttgg cctctactcc agtaaacctg attgggtttg ttcactctct | 5460 |
| gaatgattat tagccagact tcaaaattat tttatagccc aaattataac atctattgta | 5520 |
| ttatttagac ttttaacata tagagctatt tctactgatt tttgcccttg ttctgtcctt | 5580 |
| tttttcaaaa aagaaaatgt gttttttgtt tggtaccata gtgtgaaatg ctgggaacaa | 5640 |
| tgactataag acatgctatg gcacatatat ttatagtctg tttatgtaga aacaaatgta | 5700 |
| atatattaaa gccttatata taatgaactt tgtactattc acattttgta tcagtattat | 5760 |
| gtagcataac aaaggtcata atgctttcag caattgatgt cattttatta aagaacattg | 5820 |
| aaaaacttga | 5830 |

```
<210> SEQ ID NO 8
<211> LENGTH: 19
<212> TYPE: DNA
<213> ORGANISM: Artificial Sequence
<220> FEATURE:
<223> OTHER INFORMATION: Targeting Sequence

<400> SEQUENCE: 8
tcatcacgaa gtggtgaag                                                19

<210> SEQ ID NO 9
<211> LENGTH: 21
<212> TYPE: RNA
<213> ORGANISM: Artificial Sequence
<220> FEATURE:
<223> OTHER INFORMATION: Sense strand

<400> SEQUENCE: 9
ucaucacgaa guggugaagu u                                             21

<210> SEQ ID NO 10
<211> LENGTH: 21
<212> TYPE: RNA
<213> ORGANISM: Artificial Sequence
<220> FEATURE:
<223> OTHER INFORMATION: Antisense strand

<400> SEQUENCE: 10
cuucaccacu ucgugaugau u                                             21

<210> SEQ ID NO 11
<211> LENGTH: 21
<212> TYPE: DNA
<213> ORGANISM: Artificial Sequence
<220> FEATURE:
<223> OTHER INFORMATION: Sense strand
<220> FEATURE:
<221> NAME/KEY: misc_RNA
<222> LOCATION: (1)...(19)
<223> OTHER INFORMATION: ribonucleotide
<220> FEATURE:
<221> NAME/KEY: misc_feature
<222> LOCATION: (20)...(21)
<223> OTHER INFORMATION: deoxyribonucleotide

<400> SEQUENCE: 11
ucaucacgaa guggugaagt t                                             21
```

```
<210> SEQ ID NO 12
<211> LENGTH: 21
<212> TYPE: DNA
<213> ORGANISM: Artificial Sequence
<220> FEATURE:
<223> OTHER INFORMATION: Antisense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 12
cuucaccacu ucgugaugat t                                      21

<210> SEQ ID NO 13
<211> LENGTH: 21
<212> TYPE: DNA
<213> ORGANISM: Artificial Sequence
<220> FEATURE:
<223> OTHER INFORMATION: Targeting Sequence

<400> SEQUENCE: 13
aacgtacttg cagatgtgac a                                      21

<210> SEQ ID NO 14
<211> LENGTH: 19
<212> TYPE: DNA
<213> ORGANISM: Artificial Sequence
<220> FEATURE:
<223> OTHER INFORMATION: Targeting Sequence

<400> SEQUENCE: 14
gttcatggat gtctatcag                                         19

<210> SEQ ID NO 15
<211> LENGTH: 19
<212> TYPE: DNA
<213> ORGANISM: Artificial Sequence
<220> FEATURE:
<223> OTHER INFORMATION: Targeting Sequence

<400> SEQUENCE: 15
tcgagaccct ggtggacat                                         19

<210> SEQ ID NO 16
<211> LENGTH: 19
<212> TYPE: DNA
<213> ORGANISM: Artificial Sequence
<220> FEATURE:
<223> OTHER INFORMATION: Targeting Sequence

<400> SEQUENCE: 16
tgacgagggc ctggagtgt                                         19

<210> SEQ ID NO 17
<211> LENGTH: 19
<212> TYPE: DNA
<213> ORGANISM: Artificial Sequence
<220> FEATURE:
<223> OTHER INFORMATION: Targeting Sequence

<400> SEQUENCE: 17
tgacgagggc ctggagtgt                                         19
```

```
<210> SEQ ID NO 18
<211> LENGTH: 19
<212> TYPE: DNA
<213> ORGANISM: Artificial Sequence
<220> FEATURE:
<223> OTHER INFORMATION: Targeting Sequence

<400> SEQUENCE: 18
catcaccatg cagattatg                                                  19

<210> SEQ ID NO 19
<211> LENGTH: 19
<212> TYPE: DNA
<213> ORGANISM: Artificial Sequence
<220> FEATURE:
<223> OTHER INFORMATION: Targeting Sequence

<400> SEQUENCE: 19
acctcaccaa ggccagcac                                                  19

<210> SEQ ID NO 20
<211> LENGTH: 19
<212> TYPE: DNA
<213> ORGANISM: Artificial Sequence
<220> FEATURE:
<223> OTHER INFORMATION: Targeting Sequence

<400> SEQUENCE: 20
ggccagcaca taggagaga                                                  19

<210> SEQ ID NO 21
<211> LENGTH: 19
<212> TYPE: DNA
<213> ORGANISM: Artificial Sequence
<220> FEATURE:
<223> OTHER INFORMATION: Targeting Sequence

<400> SEQUENCE: 21
caaatgtgaa tgcagacca                                                  19

<210> SEQ ID NO 22
<211> LENGTH: 19
<212> TYPE: DNA
<213> ORGANISM: Artificial Sequence
<220> FEATURE:
<223> OTHER INFORMATION: Targeting Sequence

<400> SEQUENCE: 22
atgtgaatgc agaccaaag                                                  19

<210> SEQ ID NO 23
<211> LENGTH: 19
<212> TYPE: DNA
<213> ORGANISM: Artificial Sequence
<220> FEATURE:
<223> OTHER INFORMATION: Targeting Sequence

<400> SEQUENCE: 23
tgcagaccaa agaaagata                                                  19

<210> SEQ ID NO 24
<211> LENGTH: 19
<212> TYPE: DNA
<213> ORGANISM: Artificial Sequence
<220> FEATURE:
<223> OTHER INFORMATION: Targeting Sequence
```

<400> SEQUENCE: 24
agaaagatag agcaagaca                                              19

<210> SEQ ID NO 25
<211> LENGTH: 19
<212> TYPE: DNA
<213> ORGANISM: Artificial Sequence
<220> FEATURE:
<223> OTHER INFORMATION: Targeting Sequence

<400> SEQUENCE: 25
gaaagataga gcaagacaa                                              19

<210> SEQ ID NO 26
<211> LENGTH: 19
<212> TYPE: DNA
<213> ORGANISM: Artificial Sequence
<220> FEATURE:
<223> OTHER INFORMATION: Targeting Sequence

<400> SEQUENCE: 26
gatagagcaa gacaagaaa                                              19

<210> SEQ ID NO 27
<211> LENGTH: 19
<212> TYPE: DNA
<213> ORGANISM: Artificial Sequence
<220> FEATURE:
<223> OTHER INFORMATION: Targeting Sequence

<400> SEQUENCE: 27
gacaagaaaa tccctgtgg                                              19

<210> SEQ ID NO 28
<211> LENGTH: 19
<212> TYPE: DNA
<213> ORGANISM: Artificial Sequence
<220> FEATURE:
<223> OTHER INFORMATION: Targeting Sequence

<400> SEQUENCE: 28
gaaaatccct gtgggcctt                                              19

<210> SEQ ID NO 29
<211> LENGTH: 19
<212> TYPE: DNA
<213> ORGANISM: Artificial Sequence
<220> FEATURE:
<223> OTHER INFORMATION: Targeting Sequence

<400> SEQUENCE: 29
aatccctgtg ggccttgct                                              19

<210> SEQ ID NO 30
<211> LENGTH: 19
<212> TYPE: DNA
<213> ORGANISM: Artificial Sequence
<220> FEATURE:
<223> OTHER INFORMATION: Targeting Sequence

<400> SEQUENCE: 30
tccctgtggg ccttgctca                                              19

```
<210> SEQ ID NO 31
<211> LENGTH: 19
<212> TYPE: DNA
<213> ORGANISM: Artificial Sequence
<220> FEATURE:
<223> OTHER INFORMATION: Targeting Sequence

<400> SEQUENCE: 31
gcatttgttt gtacaagat                                                  19

<210> SEQ ID NO 32
<211> LENGTH: 19
<212> TYPE: DNA
<213> ORGANISM: Artificial Sequence
<220> FEATURE:
<223> OTHER INFORMATION: Targeting Sequence

<400> SEQUENCE: 32
gatccgcaga cgtgtaaat                                                  19

<210> SEQ ID NO 33
<211> LENGTH: 19
<212> TYPE: DNA
<213> ORGANISM: Artificial Sequence
<220> FEATURE:
<223> OTHER INFORMATION: Targeting Sequence

<400> SEQUENCE: 33
atgttcctgc aaaaacaca                                                  19

<210> SEQ ID NO 34
<211> LENGTH: 19
<212> TYPE: DNA
<213> ORGANISM: Artificial Sequence
<220> FEATURE:
<223> OTHER INFORMATION: Targeting Sequence

<400> SEQUENCE: 34
tgttcctgca aaaacacag                                                  19

<210> SEQ ID NO 35
<211> LENGTH: 19
<212> TYPE: DNA
<213> ORGANISM: Artificial Sequence
<220> FEATURE:
<223> OTHER INFORMATION: Targeting Sequence

<400> SEQUENCE: 35
aaacacagac tcgcgttgc                                                  19

<210> SEQ ID NO 36
<211> LENGTH: 19
<212> TYPE: DNA
<213> ORGANISM: Artificial Sequence
<220> FEATURE:
<223> OTHER INFORMATION: Targeting Sequence

<400> SEQUENCE: 36
aacacagact cgcgttgca                                                  19

<210> SEQ ID NO 37
<211> LENGTH: 19
<212> TYPE: DNA
<213> ORGANISM: Artificial Sequence
<220> FEATURE:
<223> OTHER INFORMATION: Targeting Sequence
```

```
<400> SEQUENCE: 37
acacagactc gcgttgcaa                                               19

<210> SEQ ID NO 38
<211> LENGTH: 19
<212> TYPE: DNA
<213> ORGANISM: Artificial Sequence
<220> FEATURE:
<223> OTHER INFORMATION: Targeting Sequence

<400> SEQUENCE: 38
cacagactcg cgttgcaag                                               19

<210> SEQ ID NO 39
<211> LENGTH: 19
<212> TYPE: DNA
<213> ORGANISM: Artificial Sequence
<220> FEATURE:
<223> OTHER INFORMATION: Targeting Sequence

<400> SEQUENCE: 39
ggcgaggcag cttgagtta                                               19

<210> SEQ ID NO 40
<211> LENGTH: 19
<212> TYPE: DNA
<213> ORGANISM: Artificial Sequence
<220> FEATURE:
<223> OTHER INFORMATION: Targeting Sequence

<400> SEQUENCE: 40
acgaacgtac ttgcagatg                                               19

<210> SEQ ID NO 41
<211> LENGTH: 19
<212> TYPE: DNA
<213> ORGANISM: Artificial Sequence
<220> FEATURE:
<223> OTHER INFORMATION: Targeting Sequence

<400> SEQUENCE: 41
cgaacgtact tgcagatgt                                               19

<210> SEQ ID NO 42
<211> LENGTH: 19
<212> TYPE: DNA
<213> ORGANISM: Artificial Sequence
<220> FEATURE:
<223> OTHER INFORMATION: Targeting Sequence

<400> SEQUENCE: 42
cgtacttgca gatgtgaca                                               19

<210> SEQ ID NO 43
<211> LENGTH: 19
<212> TYPE: DNA
<213> ORGANISM: Artificial Sequence
<220> FEATURE:
<223> OTHER INFORMATION: Targeting Sequence

<400> SEQUENCE: 43
gtggtcccag gctgcaccc                                               19
```

```
<210> SEQ ID NO 44
<211> LENGTH: 19
<212> TYPE: DNA
<213> ORGANISM: Artificial Sequence
<220> FEATURE:
<223> OTHER INFORMATION: Targeting Sequence

<400> SEQUENCE: 44
ggaggagggc agaatcatc                                                  19

<210> SEQ ID NO 45
<211> LENGTH: 19
<212> TYPE: DNA
<213> ORGANISM: Artificial Sequence
<220> FEATURE:
<223> OTHER INFORMATION: Targeting Sequence

<400> SEQUENCE: 45
gtggtgaagt tcatggatg                                                  19

<210> SEQ ID NO 46
<211> LENGTH: 21
<212> TYPE: DNA
<213> ORGANISM: Artificial Sequence
<220> FEATURE:
<223> OTHER INFORMATION: Targeting Sequence

<400> SEQUENCE: 46
aatcatcacg aagtggtgaa g                                               21

<210> SEQ ID NO 47
<211> LENGTH: 21
<212> TYPE: DNA
<213> ORGANISM: Artificial Sequence
<220> FEATURE:
<223> OTHER INFORMATION: Targeting Sequence

<400> SEQUENCE: 47
aagttcatgg atgtctatca g                                               21

<210> SEQ ID NO 48
<211> LENGTH: 21
<212> TYPE: DNA
<213> ORGANISM: Artificial Sequence
<220> FEATURE:
<223> OTHER INFORMATION: Targeting Sequence

<400> SEQUENCE: 48
aatcgagacc ctggtggaca t                                               21

<210> SEQ ID NO 49
<211> LENGTH: 21
<212> TYPE: DNA
<213> ORGANISM: Artificial Sequence
<220> FEATURE:
<223> OTHER INFORMATION: Targeting Sequence

<400> SEQUENCE: 49
aatgacgagg gcctggagtg t                                               21

<210> SEQ ID NO 50
<211> LENGTH: 21
<212> TYPE: DNA
<213> ORGANISM: Artificial Sequence
<220> FEATURE:
<223> OTHER INFORMATION: Targeting Sequence
```

-continued

```
<400> SEQUENCE: 50
aacatcacca tgcagattat g                                          21

<210> SEQ ID NO 51
<211> LENGTH: 21
<212> TYPE: DNA
<213> ORGANISM: Artificial Sequence
<220> FEATURE:
<223> OTHER INFORMATION: Targeting Sequence

<400> SEQUENCE: 51
aaacctcacc aaggccagca c                                          21

<210> SEQ ID NO 52
<211> LENGTH: 21
<212> TYPE: DNA
<213> ORGANISM: Artificial Sequence
<220> FEATURE:
<223> OTHER INFORMATION: Targeting Sequence

<400> SEQUENCE: 52
aaggccagca cataggagag a                                          21

<210> SEQ ID NO 53
<211> LENGTH: 21
<212> TYPE: DNA
<213> ORGANISM: Artificial Sequence
<220> FEATURE:
<223> OTHER INFORMATION: Targeting Sequence

<400> SEQUENCE: 53
aacaaatgtg aatgcagacc a                                          21

<210> SEQ ID NO 54
<211> LENGTH: 21
<212> TYPE: DNA
<213> ORGANISM: Artificial Sequence
<220> FEATURE:
<223> OTHER INFORMATION: Targeting Sequence

<400> SEQUENCE: 54
aaatgtgaat gcagaccaaa g                                          21

<210> SEQ ID NO 55
<211> LENGTH: 21
<212> TYPE: DNA
<213> ORGANISM: Artificial Sequence
<220> FEATURE:
<223> OTHER INFORMATION: Targeting Sequence

<400> SEQUENCE: 55
aatgcagacc aaagaaagat a                                          21

<210> SEQ ID NO 56
<211> LENGTH: 21
<212> TYPE: DNA
<213> ORGANISM: Artificial Sequence
<220> FEATURE:
<223> OTHER INFORMATION: Targeting Sequence

<400> SEQUENCE: 56
aaagaaagat agagcaagac a                                          21
```

<210> SEQ ID NO 57
<211> LENGTH: 21
<212> TYPE: DNA
<213> ORGANISM: Artificial Sequence
<220> FEATURE:
<223> OTHER INFORMATION: Targeting Sequence

<400> SEQUENCE: 57
aagaaagata gagcaagaca a                                              21

<210> SEQ ID NO 58
<211> LENGTH: 23
<212> TYPE: DNA
<213> ORGANISM: Artificial Sequence
<220> FEATURE:
<223> OTHER INFORMATION: Targeting Sequence

<400> SEQUENCE: 58
aagatagagc aagacaagaa aat                                            23

<210> SEQ ID NO 59
<211> LENGTH: 23
<212> TYPE: DNA
<213> ORGANISM: Artificial Sequence
<220> FEATURE:
<223> OTHER INFORMATION: Targeting Sequence

<400> SEQUENCE: 59
aagacaagaa aatccctgtg ggc                                            23

<210> SEQ ID NO 60
<211> LENGTH: 23
<212> TYPE: DNA
<213> ORGANISM: Artificial Sequence
<220> FEATURE:
<223> OTHER INFORMATION: Targeting Sequence

<400> SEQUENCE: 60
aagaaaatcc ctgtgggcct tgc                                            23

<210> SEQ ID NO 61
<211> LENGTH: 23
<212> TYPE: DNA
<213> ORGANISM: Artificial Sequence
<220> FEATURE:
<223> OTHER INFORMATION: Targeting Sequence

<400> SEQUENCE: 61
aatccctgtg ggccttgctc aga                                            23

<210> SEQ ID NO 62
<211> LENGTH: 23
<212> TYPE: DNA
<213> ORGANISM: Artificial Sequence
<220> FEATURE:
<223> OTHER INFORMATION: Targeting Sequence

<400> SEQUENCE: 62
aagcatttgt ttgtacaaga tcc                                            23

<210> SEQ ID NO 63
<211> LENGTH: 23
<212> TYPE: DNA
<213> ORGANISM: Artificial Sequence
<220> FEATURE:
<223> OTHER INFORMATION: Targeting Sequence

```
<400> SEQUENCE: 63
aagatccgca gacgtgtaaa tgt                                          23

<210> SEQ ID NO 64
<211> LENGTH: 23
<212> TYPE: DNA
<213> ORGANISM: Artificial Sequence
<220> FEATURE:
<223> OTHER INFORMATION: Targeting Sequence

<400> SEQUENCE: 64
aaatgttcct gcaaaaacac aga                                          23

<210> SEQ ID NO 65
<211> LENGTH: 23
<212> TYPE: DNA
<213> ORGANISM: Artificial Sequence
<220> FEATURE:
<223> OTHER INFORMATION: Targeting Sequence

<400> SEQUENCE: 65
aatgttcctg caaaaacaca gac                                          23

<210> SEQ ID NO 66
<211> LENGTH: 23
<212> TYPE: DNA
<213> ORGANISM: Artificial Sequence
<220> FEATURE:
<223> OTHER INFORMATION: Targeting Sequence

<400> SEQUENCE: 66
aaaaacacag actcgcgttg caa                                          23

<210> SEQ ID NO 67
<211> LENGTH: 23
<212> TYPE: DNA
<213> ORGANISM: Artificial Sequence
<220> FEATURE:
<223> OTHER INFORMATION: Targeting Sequence

<400> SEQUENCE: 67
aaaacacaga ctcgcgttgc aag                                          23

<210> SEQ ID NO 68
<211> LENGTH: 23
<212> TYPE: DNA
<213> ORGANISM: Artificial Sequence
<220> FEATURE:
<223> OTHER INFORMATION: Targeting Sequence

<400> SEQUENCE: 68
aaacacagac tcgcgttgca agg                                          23

<210> SEQ ID NO 69
<211> LENGTH: 23
<212> TYPE: DNA
<213> ORGANISM: Artificial Sequence
<220> FEATURE:
<223> OTHER INFORMATION: Targeting Sequence

<400> SEQUENCE: 69
aacacagact cgcgttgcaa ggc                                          23
```

<210> SEQ ID NO 70
<211> LENGTH: 23
<212> TYPE: DNA
<213> ORGANISM: Artificial Sequence
<220> FEATURE:
<223> OTHER INFORMATION: Targeting Sequence

<400> SEQUENCE: 70
aaggcgaggc agcttgagtt aaa                                            23

<210> SEQ ID NO 71
<211> LENGTH: 23
<212> TYPE: DNA
<213> ORGANISM: Artificial Sequence
<220> FEATURE:
<223> OTHER INFORMATION: Targeting Sequence

<400> SEQUENCE: 71
aaacgaacgt acttgcagat gtg                                            23

<210> SEQ ID NO 72
<211> LENGTH: 23
<212> TYPE: DNA
<213> ORGANISM: Artificial Sequence
<220> FEATURE:
<223> OTHER INFORMATION: Targeting Sequence

<400> SEQUENCE: 72
aacgaacgta cttgcagatg tga                                            23

<210> SEQ ID NO 73
<211> LENGTH: 23
<212> TYPE: DNA
<213> ORGANISM: Artificial Sequence
<220> FEATURE:
<223> OTHER INFORMATION: Targeting Sequence

<400> SEQUENCE: 73
aagtggtccc aggctgcacc cat                                            23

<210> SEQ ID NO 74
<211> LENGTH: 23
<212> TYPE: DNA
<213> ORGANISM: Artificial Sequence
<220> FEATURE:
<223> OTHER INFORMATION: Targeting Sequence

<400> SEQUENCE: 74
aaggaggagg gcagaatcat cac                                            23

<210> SEQ ID NO 75
<211> LENGTH: 23
<212> TYPE: DNA
<213> ORGANISM: Artificial Sequence
<220> FEATURE:
<223> OTHER INFORMATION: Targeting Sequence

<400> SEQUENCE: 75
aagtggtgaa gttcatggat gtc                                            23

<210> SEQ ID NO 76
<211> LENGTH: 23
<212> TYPE: DNA
<213> ORGANISM: Artificial Sequence
<220> FEATURE:
<223> OTHER INFORMATION: Targeting Sequence

```
<400> SEQUENCE: 76
aaaatccctg tgggccttgc tca                                          23

<210> SEQ ID NO 77
<211> LENGTH: 21
<212> TYPE: DNA
<213> ORGANISM: Artificial Sequence
<220> FEATURE:
<223> OTHER INFORMATION: Sense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 77
accucaccaa ggccagcact t                                            21

<210> SEQ ID NO 78
<211> LENGTH: 21
<212> TYPE: DNA
<213> ORGANISM: Artificial Sequence
<220> FEATURE:
<223> OTHER INFORMATION: Antisense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 78
gugcuggccu uggugaggut t                                            21

<210> SEQ ID NO 79
<211> LENGTH: 18
<212> TYPE: DNA
<213> ORGANISM: Artificial Sequence
<220> FEATURE:
<223> OTHER INFORMATION: Targeting sequence

<400> SEQUENCE: 79
ggctacgtcc agcgcacc                                                18

<210> SEQ ID NO 80
<211> LENGTH: 21
<212> TYPE: DNA
<213> ORGANISM: Artificial Sequence
<220> FEATURE:
<223> OTHER INFORMATION: Targeting sequence

<400> SEQUENCE: 80
aaaccucacc aaagccagca c                                            21

<210> SEQ ID NO 81
<211> LENGTH: 21
<212> TYPE: DNA
<213> ORGANISM: Artificial
<220> FEATURE:
<223> OTHER INFORMATION: Targeting Sequence

<400> SEQUENCE: 81
aaggaggagg gcagaatcat c                                            21
```

-continued

```
<210> SEQ ID NO 82
<211> LENGTH: 21
<212> TYPE: DNA
<213> ORGANISM: Artificial
<220> FEATURE:
<223> OTHER INFORMATION: Targeting Sequence

<400> SEQUENCE: 82
aatgtgaatg cagaccaaag a                                              21

<210> SEQ ID NO 83
<211> LENGTH: 21
<212> TYPE: DNA
<213> ORGANISM: Artificial
<220> FEATURE:
<223> OTHER INFORMATION: Targeting Sequence

<400> SEQUENCE: 83
aaagcatttg tttgtacaag a                                              21

<210> SEQ ID NO 84
<211> LENGTH: 21
<212> TYPE: DNA
<213> ORGANISM: Artificial
<220> FEATURE:
<223> OTHER INFORMATION: Targeting Sequence

<400> SEQUENCE: 84
aagatccgca gacgtgtaaa t                                              21

<210> SEQ ID NO 85
<211> LENGTH: 21
<212> TYPE: DNA
<213> ORGANISM: Artificial
<220> FEATURE:
<223> OTHER INFORMATION: Targeting Sequence

<400> SEQUENCE: 85
aaacacacac tcgcgttgca a                                              21
```

COMPOSITIONS AND METHODS FOR SIRNA INHIBITION OF ANGIOGENESIS

CROSS REFERENCE TO RELATED APPLICATION

This application is a continuation-in-part of U.S. application Ser. No. 10/294,228 filed on Nov. 14, 2002, now U.S. Pat. No. 7,148,342, which claims the benefit of U.S. provisional patent application Ser. No. 60/398,417, filed on Jul. 24, 2002.

REFERENCE TO GOVERNMENT GRANT

The invention described herein was supported in part by NIH/NEI grant no. R01-EY10820, EY-13410 and EY12156. The U.S. government has certain rights in this invention.

JOINT RESEARCH AGREEMENT

Not applicable

FIELD OF THE INVENTION

Not applicable

BACKGROUND OF THE INVENTION

Not applicable

Angiogenesis, defined as the growth of new capillary blood vessels or "neovascularization," plays a fundamental role in growth and development. In mature humans, the ability to initiate angiogenesis is present in all tissues, but is held under strict control. A key regulator of angiogenesis is vascular endothelial growth factor ("VEGF"), also called vascular permeability factor ("VPF"). VEGF exists in at least four different alternative splice forms in humans ($VEGF_{121}$, $VEGF_{165}$, $VEGF_{189}$ and $VEGF_{206}$), all of which exert similar biological activities.

Angiogenesis is initiated when secreted VEGF binds to the Flt-1 and Flk-1/KDR receptors (also called VEGF receptor 1 and VEGF receptor 2), which are expressed on the surface of endothelial cells. Flt-1 and Flk-1/KDR are transmembrane protein tyrosine kinases, and binding of VEGF initiates a cell signal cascade resulting in the ultimate neovascularization in the surrounding tissue.

Aberrant angiogenesis, or the pathogenic growth of new blood vessels, is implicated in a number of conditions. Among these conditions are diabetic retinopathy, diabetic macular edema (DME), psoriasis, exudative or "wet" age-related macular degeneration ("ARMD"), rheumatoid arthritis and other inflammatory diseases, and most cancers. The diseases associated with these conditions exhibit abnormally high levels of VEGF, and generally show a high degree of vascularization or vascular permeability.

ARMD in particular is a clinically important angiogenic disease. This condition is characterized by choroidal neovascularization in one or both eyes in aging individuals, and is the major cause of blindness in industrialized countries.

Diabetic macular edema (DME), also called diabetic retinopathy, is a complication of the chronically high blood sugar afflicting diabetics. It is caused by leakiness of retinal blood vessels and the growth of new blood vessels on the retina, optic nerve and the iris. The leaky blood vessels result in swelling of the retina and visual loss. The new blood vessels that grow on the optic nerve and retina can also bleed, resulting in severe visual loss. In addition, new blood vessels in the iris clog the drain of the eye and can result in extremely high pressure in the eye with accompanying intense pain and the potential loss of the eye. DME can affect almost anyone with diabetes. In general, the longer someone has diabetes, the greater the risk of developing DME. Eventually, almost everyone with juvenile-onset diabetes will develop some symptoms of DME. Those who acquire diabetes later in life are also at risk of DME, although they are somewhat less likely to develop advanced DME.

A number of therapeutic strategies exist for inhibiting aberrant angiogenesis, which attempt to reduce the production or effect of VEGF. For example, anti-VEGF or anti-VEGF receptor antibodies (Kim E S et al. (2002), *PNAS USA* 99: 11399-11404), and soluble VEGF "traps" which compete with endothelial cell receptors for VEGF binding (Holash J et al. (2002), *PNAS USA* 99: 11393-11398) have been developed. Classical VEGF "antisense" or aptamer therapies directed against VEGF gene expression have also been proposed (U.S. published application 2001/0021772 of Uhlmann et al.). However, the anti-angiogenic agents used in these therapies can produce only a stoichiometric reduction in VEGF or VEGF receptor, and the agents are typically overwhelmed by the abnormally high production of VEGF by the diseased tissue. The results achieved with available anti-angiogenic therapies have therefore been unsatisfactory.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), *Nature* 391: 806-811). These short, dsRNA molecules, called "short interfering RNA" or "siRNA," cause the destruction of messenger RNAs ("mRNAs") which share sequence homology with the siRNA to within one nucleotide resolution (Elbashir S M et al. (2001), *Genes Dev*, 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

What is needed, therefore, are agents which selectively inhibit expression of VEGF or VEGF receptors in catalytic or sub-stoichiometric amounts.

SUMMARY OF THE INVENTION

One embodiment of the present invention is directed to siRNAs that specifically target and cause RNAi-induced degradation of mRNA from VEGF, Flt-1 and Flk-1/KDR genes. The siRNA compounds and compositions are used to inhibit angiogenesis, in particular for the treatment of cancerous tumors, age-related macular degeneration, and other angiogenic diseases.

Another embodiment of the present invention provides an isolated siRNA which targets human VEGF mRNA, human Flt-1 mRNA, human Flk-1/KDR mRNA, or an alternative splice form, mutant or cognate thereof. The siRNA comprises a sense RNA strand and an antisense RNA strand which form an RNA duplex. The sense RNA strand comprises a nucleotide sequence identical to a target sequence of about 19 to about 25 contiguous nucleotides in the target mRNA.

In another embodiment of the present invention, recombinant plasmids and viral vectors which express the siRNA, as well as pharmaceutical compositions comprising the siRNA and a pharmaceutically acceptable carrier are provided.

Further embodiments of the present invention provide methods of inhibiting expression of human VEGF mRNA, human Flt-1 mRNA, human Flk-1/KDR mRNA, or an alternative splice form, mutant or cognate thereof, comprising administering to a subject an effective amount of the siRNA such that the target mRNA is degraded.

Other embodiments of the present invention provide methods of inhibiting angiogenesis and treating angiogenic diseases in a subject, comprising administering to a subject an effective amount of an siRNA targeted to human VEGF mRNA, human Flt-1 mRNA, human Flk-1/KDR mRNA, or an alternative splice form, mutant or cognate thereof.

DETAILED DESCRIPTION OF THE INVENTION

Figure 1A:
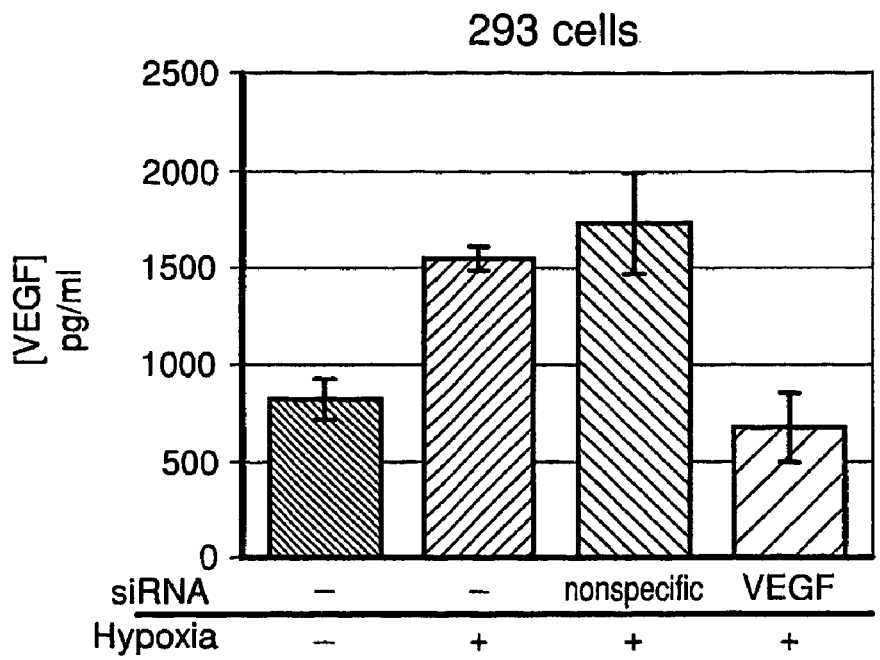
FIGS. 1A and 1B are a histograms of VEGF concentration (in pg/ml) in hypoxic 293 and HeLa cells treated with no siRNA ("-"); nonspecific siRNA ("nonspecific"); or siRNA targeting human VEGF mRNA ("VEGF"). VEGF concentration (in pg/ml) in non-hypoxic 293 and HeLa cells is also shown. Each bar represents the average of four experiments, and the error is the standard deviation of the mean.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "molecule" is a reference to one or more molecules and equivalents thereof known to those skilled in the art, and so forth. As used herein, the term "about" means plus or minus 10% of the numerical value of the number with which it is being used. Therefore, about 50% means in the range of 45%-55%.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the progression of angiogenesis in a subject.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

As used herein, "target mRNA" means human VEGF, Flt-1 or Flk-1/KDR mRNA, mutant or alternative splice forms of human VEGF, Flt-1 or Flk-1/KDR mRNA, or mRNA from cognate VEGF, Flt-1 or Flk-1/KDR genes.

As used herein, a gene or mRNA which is "cognate" to human VEGF, Flt-1 or Flk-1/KDR is a gene or mRNA from another mammalian species which is homologous to human VEGF, Flt-1 or Flk-1/KDR. For example, the cognate VEGF mRNA from the mouse is given in SEQ ID NO: 1.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to VEGF, Flt-1 or Flk-1/KDR mRNA are advantageously used to inhibit angiogenesis, in particular for the treatment of angiogenic disease. The siRNA are believed to cause the RNAi-mediated degradation of these mRNAs, so that the protein product of the VEGF, Flt-1 or Flk-1/KDR genes is not produced or is produced in reduced amounts. Because VEGF binding to the Flt-1 or Flk-1/KDR receptors is required for initiating and maintaining angiogenesis, the siRNA-mediated degradation of VEGF, Flt-1 or Flk-1/KDR mRNA inhibits the angiogenic process.

One aspect of the present invention therefore provides isolated siRNA comprising short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is identical to a target sequence contained within the target mRNA.

The sense and antisense strands of the siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules (see Tuschl, T. (2002), supra).

Splice variants of human VEGF are known, including $VEGF_{121}$ (SEQ ID NO: 2), $VEGF_{165}$ (SEQ ID NO: 3), $VEGF_{189}$ (SEQ ID NO: 4) and $VEGF_{206}$ (SEQ ID NO: 5). The mRNA transcribed from the human VEGF, Flt-1 (SEQ ID NO: 6) or Flk-1/KDR (SEQ ID NO: 7) genes can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the VEGF, Flt-1 or Flk-1/KDR genes can be used to query such a database to determine whether ESTs representing alternatively spliced mRNAs have been found for a these genes.

A technique called "RNAse protection" can also be used to identify alternatively spliced VEGF, Flt-1 or Flk-1/KDR mRNAs. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced VEGF, Flt-1 or Flk-1/KDR mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

mRNA produced from mutant VEGF, Flt-1 or Flk-1/KDR genes can also be readily identified through the techniques described above for identifying alternative splice forms. As used herein, "mutant" VEGF, Flt-1 or Flk-1/KDR genes or mRNA include human VEGF, Flt-1 or Flk-1/KDR genes or mRNA which differ in sequence from the VEGF, Flt-1 or Flk-1/KDR sequences set forth herein. Thus, allelic forms of these genes, and the mRNA produced from them, are considered "mutants" for purposes of this invention.

It is understood that human VEGF, Flt-1 or Flk-1/KDR mRNA may contain target sequences in common with their respective alternative splice forms, cognates or mutants. A single siRNA comprising such a common targeting sequence can therefore induce RNAi-mediated degradation of different RNA types which contain the common targeting sequence.

The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA can also comprise a 3' overhang. As used herein, a "3' overhang" refers to at least one unpaired nucleotide extending from the 3'-end of a duplexed RNA strand.

Thus in one embodiment, the siRNA comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In a further embodiment, the siRNA comprises a sequence having no more than five (5) consecutive purines or pyrimidines. In a further embodiment, the siRNA comprises a sequence having no more than five (5) consecutive nucleotides having the same nucleobase (i.e., A, C, G, or U/T).

The siRNA can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon (see, e.g., the target sequences of SEQ ID NOS: 73 and 74 in Table 1 below, which are within 100 nt of the 5'-end of the $VEGF_{121}$ cDNA.

In a further embodiment of the present invention, the target mRNA sequence comprises no more than five (5) consecutive purines or pyrimidines. For example, a suitable target sequence in the $VEGF_{121}$ cDNA sequence is:

TCATCACGAAGTGGTGAAG    (SEQ ID NO: 8)

Thus, an siRNA targeting this sequence, and which has 3' uu overhangs on each strand (overhangs shown in bold), is:

5'-ucaucacgaaguggugaaguu-3'    (SEQ ID NO: 9)

3'-uuaguagugcuucaccacuuc-5'    (SEQ ID NO: 10)

An siRNA targeting this same sequence, but having 3' TT overhangs on each strand (overhangs shown in bold) is:

5'-ucaucacgaaguggugaagTT-3'    (SEQ ID NO: 11)

3'-TTaguagugcuucaccacuuc-5'    (SEQ ID NO: 12)

Other $VEGF_{121}$ target sequences from which siRNA can be derived are given in Table 1. It is understood that all $VEGF_{121}$ target sequences listed in Table 1 are within that portion of the $VEGF_{121}$ alternative splice form which is common to all human VEGF alternative splice forms. Thus, the $VEGF_{121}$ target sequences in Table 1 can also target $VEGF_{165}$, $VEGF_{189}$ and $VEGF_{206}$ mRNA. Target sequences which target a specific VEGF isoform can also be readily identified. For example, a target sequence which targets $VEGF_{165}$ mRNA but not $VEGF_{121}$ mRNA is AACGTACTTGCAGAT-GTGACA (SEQ ID NO: 13). Exemplary target sequences for human Flt-1 for human Flk-1/KDR are given in PCT/US2003/0022444 filed Jul. 18, 2003, herein incorporated by reference in its entirety.

TABLE 1

VEGF Target Sequences

| target sequence | SEQ ID NO: |
|---|---|
| cognate VEGF mRNA sequence | 1 |
| Splice variant $VEGF_{121}$ sequence | 2 |
| Splice variant $VEGF_{165}$ sequence | 3 |
| Splice variant $VEGF_{189}$ sequence | 4 |
| Splice variant $VEGF_{206}$ sequence | 5 |
| TCATCACGAAGTGGTGAAG | 8 |
| ucaucacgaaguggugaaguu | 9 |
| uuaguagugcuucaccacuuc | 10 |
| ucaucacgaaguggugaagTT | 11 |
| TTaguagugcuucaccacuuc | 12 |
| AACGTACTTGCAGATGTGACA | 13 |
| GTTCATGGATGTCTATCAG | 14 |
| TCGAGACCCTGGTGGACAT | 15 |
| TGACGAGGGCCTGGAGTGT | 16 |
| TGACGAGGGCCTGGAGTGT | 17 |
| CATCACCATGCAGATTATG | 18 |
| ACCTCACCAAGGCCAGCAC | 19 |
| GGCCAGCACATAGGAGAGA | 20 |
| CAAATGTGAATGCAGACCA | 21 |
| ATGTGAATGCAGACCAAAG | 22 |
| TGCAGACCAAAGAAAGATA | 23 |
| AGAAAGATAGAGCAAGACA | 24 |
| GAAAGATAGAGCAAGACAA | 25 |
| GATAGAGCAAGACAAGAAA | 26 |
| GACAAGAAAATCCCTGTGG | 27 |

TABLE 1-continued

VEGF Target Sequences

| target sequence | SEQ ID NO: |
|---|---|
| GAAAATCCCTGTGGGCCTT | 28 |
| AATCCCTGTGGGCCTTGCT | 29 |
| TCCCTGTGGGCCTTGCTCA | 30 |
| GCATTTGTTTGTACAAGAT | 31 |
| GATCCGCAGACGTGTAAAT | 32 |
| ATGTTCCTGCAAAAACACA | 33 |
| TGTTCCTGCAAAAACACAG | 34 |
| AAACACAGACTCGCGTTGC | 35 |
| AACACAGACTCGCGTTGCA | 36 |
| ACACAGACTCGCGTTGCAA | 37 |
| CACAGACTCGCGTTGCAAG | 38 |
| GGCGAGGCAGCTTGAGTTA | 39 |
| ACGAACGTACTTGCAGATG | 40 |
| CGAACGTACTTGCAGATGT | 41 |
| CGTACTTGCAGATGTGACA | 42 |
| GTGGTCCCAGGCTGCACCC | 43 |
| GGAGGAGGGCAGAATCATC | 44 |
| GTGGTGAAGTTCATGGATG | 45 |
| AATCATCACGAAGTGGTGAAG | 46 |
| AAGTTCATGGATGTCTATCAG | 47 |
| AATCGAGACCCTGGTGGACAT | 48 |
| AATGACGAGGGCCTGGAGTGT | 49 |
| AACATCACCATGCAGATTATG | 50 |
| AAACCTCACCAAGGCCAGCAC | 51 |
| AAGGCCAGCACATAGGAGAGA | 52 |
| AACAAATGTGAATGCAGACCA | 53 |
| AAATGTGAATGCAGACCAAAG | 54 |
| AATGCAGACCAAAGAAAGATA | 55 |
| AAAGAAAGATAGAGCAAGACA | 56 |
| AAGAAAGATAGAGCAAGACAA | 57 |
| AAGATAGAGCAAGACAAGAAAT | 58 |
| AAGACAAGAAAATCCCTGTGGGC | 59 |
| AAGAAAATCCCTGTGGGCCTTGC | 60 |
| AATCCCTGTGGGCCTTGCTCAGA | 61 |
| AAGCATTTGTTTGTACAAGATCC | 62 |
| AAGATCCGCAGACGTGTAAATGT | 63 |
| AAATGTTCCTGCAAAAACACAGA | 64 |
| AATGTTCCTGCAAAAACACAGAC | 65 |
| AAAAACACAGACTCGCGTTGCAA | 66 |
| AAAACACAGACTCGCGTTGCAAG | 67 |
| AAACACAGACTCGCGTTGCAAGG | 68 |
| AACACAGACTCGCGTTGCAAGGC | 69 |
| AAGGCGAGGCAGCTTGAGTTAAA | 70 |
| AAACGAACGTACTTGCAGATGTG | 71 |
| AACGAACGTACTTGCAGATGTGA | 72 |
| AAGTGGTCCCAGGCTGCACCCAT | 73 |
| AAGGAGGAGGGCAGAATCATCAC | 74 |
| AAGTGGTGAAGTTCATGGATGTC | 75 |
| AAAATCCCTGTGGGCCTTGCTCA | 76 |
| accucaccaaggccagcacTT | 77 |
| gugcuggccuuggugagguTT | 78 |
| GGCTACGTCCAGCGCACC | 79 |
| AAACCUCACCAAAGCCAGCAC | 80 |

The siRNA can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, the siRNA are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo. USA), Pierce Chemical (part of Perbio Science, Rockford, Ill. USA), Glen Research (Sterling, Va. USA), ChemGenes (Ashland, Mass. USA) and Cruachem (Glasgow, UK). The siRNA can also be synthesized as multiple complementary RNA molecules, as described in more detail in U.S. Provisional Application No. 60/824,953, entitled "siRNA and Methods of Manufacture" filed simultaneously herewith, herein incorporated by reference in its entirety.

Alternatively, siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol,* 20: 446-448; Brummelkamp T R et al. (2002), *Science* 296: 550-553; Miyagishi M et al. (2002), *Nat. Biotechnol.* 20: 497-500; Paddison P J et al. (2002), *Genes Dev.* 16: 948-958; Lee N S et al. (2002), *Nat. Biotechnol.* 20: 500-505; and Paul C P et al. (2002), *Nat. Biotechnol.* 20: 505-508, the entire disclosures of which are herein incorporated by reference.

A plasmid comprising nucleic acid sequences for expressing an siRNA is described in Example 7 below. That plasmid, called pAAVsiRNA, comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA can also be expressed from recombinant viral vectors intracellularly at or near the area of neovascularization in vivo. The recombinant viral vectors of the invention comprise sequences encoding the siRNA and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA to cells in vivo is discussed in more detail below.

siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from AV and AAV. In a particularly preferred embodiment, the siRNA is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA, a method for constructing the recombinant AV vector, and a method for delivering the vector into target cells, are described in Xia H et al. (2002), *Nat. Biotech.* 20: 1006-1010.

Suitable AAV vectors for expressing the siRNA, methods for constructing the recombinant AAV vector, and methods for delivering the vectors into target cells are described in Samulski R et al. (1987), *J. Virol.* 61: 3096-3101; Fisher K J et al. (1996), *J. Virol.,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. An exemplary method for generating a recombinant AAV vector of the invention is described in Example 7 below.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of VEGF, Flt-1 or Flk-1/KDR receptor protein in the cultured cells can be measured by ELISA or Western blot. A suitable cell culture system for measuring the effect of the present siRNA on target mRNA or protein levels is described in Example 1 below.

RNAi-mediated degradation of target mRNA by an siRNA containing a given target sequence can also be evaluated with animal models of neovascularization, such as the ROP or CNV mouse models. For example, areas of neovascularization in an ROP or CNV mouse can be measured before and after administration of an siRNA. A reduction in the areas of neovascularization in these models upon administration of the siRNA indicates the down-regulation of the target mRNA (see Example 6 below).

As discussed above, the siRNA is capable of targeting and causing the RNAi-mediated degradation of VEGF, Flt-1 or Flk-1/KDR mRNA, or alternative splice forms, mutants or cognates thereof, preferably VEGF, and more preferably human VEGF. Degradation of the target mRNA by the present siRNA reduces the production of a functional gene product from the VEGF, Flt-1 or Flk-1/KDR genes. Thus, another embodiment of the present invention provides a method of inhibiting expression of VEGF, Flt-1 or Flk-1/KDR in a subject, comprising administering an effective amount of an siRNA to the subject, such that the target mRNA is degraded. As the products of the VEGF, Flt-1 and Flk-1/

KDR genes are required for initiating and maintaining angiogenesis, another embodiment of the present invention provides a method of inhibiting angiogenesis in a subject by the RNAi-mediated degradation of the target mRNA by the present siRNA.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed by ophthalmoscopy.

Inhibition of angiogenesis can also be inferred through observing a change or reversal in a pathogenic condition associated with the angiogenesis. For example, in ARMD, a slowing, halting or reversal of vision loss indicates an inhibition of angiogenesis in the choroid. For tumors, a slowing, halting-or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA.

It is understood that the siRNA can degrade the target mRNA (and thus inhibit angiogenesis) in substoichiometric amounts. Without wishing to be bound by any theory, it is believed that the siRNA causes degradation of the target mRNA in a catalytic manner. Thus, compared to standard anti-angiogenic therapies, significantly less siRNA needs to be delivered at or near the site of neovascularization to have a therapeutic effect.

One skilled in the art can readily determine an effective amount of the siRNA to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA comprises an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness.

Preferably, an siRNA is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA is used to inhibit choroidal neovascularization in age-related macular degeneration.

For treating angiogenic diseases, the siRNA can administered to a subject in combination with a pharmaceutical agent which is different from the present siRNA. Alternatively, the siRNA can be administered to a subject in combination with another therapeutic method designed to treat the angiogenic disease. For example, the siRNA can be administered in combination with therapeutic methods currently employed for treating cancer or preventing tumor metastasis (e.g., radiation therapy, chemotherapy, and surgery). For treating tumors, the siRNA is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Preferably, the liposomes encapsulating the present siRNA comprises a ligand molecule that can target the liposome to a particular cell or tissue at or near the site of angiogenesis. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), P.N.A.S., USA, 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA are also discussed above, and methods for delivering such vectors to an area of neovascularization in a patient are within the skill in the art.

The siRNA can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. More preferably, the siRNA is administered topically to the eye, e.g. in liquid or gel form to the lower eye lid or conjunctival cul-de-sac, as is within the skill in the art (see, e.g., Acheampong A A et al, 2002, Drug Metabol. and Disposition 30: 421-429, the entire disclosure of which is herein incorporated by reference).

Typically, the siRNA is administered topically to the eye in amounts of from about 5 microliters to about 75 microliters, for example from about 7 microliters to about 50 microliters, preferably from about 10 microliters to about 30 microliters. It is understood that topical instillation in the eye of siRNA in volumes greater than 75 microliters can result in loss of siRNA from the eye through spillage and drainage. Thus, it is preferable to administer a high concentration of siRNA (e.g., 100-1000 nM) in as small a volume as possible.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference. In another preferred embodiment, the siRNA is administered by intravitreal injection.

The siRNA can be administered in a single dose or in multiple doses. Where the administration of the siRNA is by infusion, the infusion can be a single sustained dose or can be delivered by multiple infusions. Injection of the agent directly into the tissue is at or near the site of neovascularization preferred. Multiple injections of the agent into the tissue at or near the site of neovascularization are particularly preferred.

One skilled in the art can also readily determine an appropriate dosage regimen for administering the siRNA to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected at or near the site of neovascularization (e.g., intravitreally) once a week for seven weeks. It is understood that periodic administrations of the siRNA for an indefinite length of time may be necessary for subjects suffering from a chronic neovascularization disease, such as wet ARMD or diabetic retinopathy.

Where a dosage regimen comprises multiple administrations, it is understood that the effective amount of siRNA administered to the subject can comprise the total amount of siRNA administered over the entire dosage regimen.

The siRNA are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 17th ed., Mack Publishing Company, Easton, Pa. (1985), the entire disclosure of which is herein incorporated by reference.

In one embodiment, the pharmaceutical formulations comprise an siRNA (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA. A pharmaceutical composition for aerosol (inhalational) administration can comprise 0.01-20% by weight, preferably 1%-10% by weight, of one or more siRNA encapsulated in a liposome as described above, and propellant. A carrier can also be included as desired; e.g., lecithin for intranasal delivery.

The invention will now be illustrated with the following non-limiting examples. The animal experiments described in Examples 4-6 and 8-9 were performed using the University of Pennsylvania institutional guidelines for the care and use of animals in research. The animal experiment described in Example 10 will be performed in accordance with the Standard Operating Procedures of Sierra Biomedical, 587 Dunn Circle, Sparks, Nev., 89431.

EXAMPLE 1 siRNA Transfection and Hypoxia Induction In Vitro siRNA Design—A 19 nt sequence located 329 nt from the 5' end of human VEGF mRNA was chosen as a target sequence: AAACCTCACCAAGGCCAGCAC (SEQ ID NO: 51). To ensure that it was not contained in the mRNA from any other genes, this target sequence was entered into the BLAST search engine provided by NCBI. The use of the BLAST algorithm is described in Altschul et al. (1990), *J. Mol. Biol.* 215: 403-410 and Altschul et al. (1997), *Nucleic Acids Res.* 25: 3389-3402, the disclosures of which are herein incorporated by reference in their entirety. As no other mRNA was found which contained the target sequence, an siRNA duplex was synthesized to target this sequence (Dharmacon Research, Inc., Lafayette, Colo.).

The siRNA duplex had the following sense and antisense strands.

```
sense:
5'-accucaccaaggccagcacTT-3'.        (SEQ ID NO: 77)

antisense:
5'-gugcuggccuuggugagguTT-3'.        (SEQ ID NO: 78)
```

Together, the siRNA sense and antisense strands formed a 19 nt double-stranded siRNA with TT 3' overhangs (shown in bold) on each strand. This siRNA was termed "Candidate 5" or "Cand5." Other siRNA which target human VEGF mRNA were designed and tested as described for Cand5.

An siRNA targeting the following sequence in green fluorescent protein (GFP) mRNA was used as a nonspecific control: GGCTACGTCCAGCGCACC (SEQ ID NO: 79). The siRNA was purchased from Dharmacon (Lafayette, Colo.).

siRNA Transfection and Hypoxia Induction In Vitro—Human cell lines (293; Hela and ARPE19) were separately seeded into 24-well plates in 250 microliters of complete DMEM medium one day prior to transfection, so that the cells were ~50% confluent at the time of transfection. Cells were transfected with 2.5 nM Cand5 siRNA, and with either no siRNA or 2.5 nM non-specific siRNA (targeting GFP) as controls. Transfections were performed in all cell lines with the "Transit TKO Transfection" reagent, as recommended by the manufacturer (Mirus).

Twenty four hours after transfection, hypoxia was induced in the cells by the addition of desferoxamide mesylate to a final concentration of 130 micromolar in each well. Twenty four hours post-transfection, the cell culture medium was removed from all wells, and a human VEGF ELISA (R&D systems, Minneapolis, Minn.) was performed on the culture medium as described in the Quantikine human VEGF ELISA protocol available from the manufacturer, the entire disclosure of which is herein incorporated by reference.

Figure 1B:
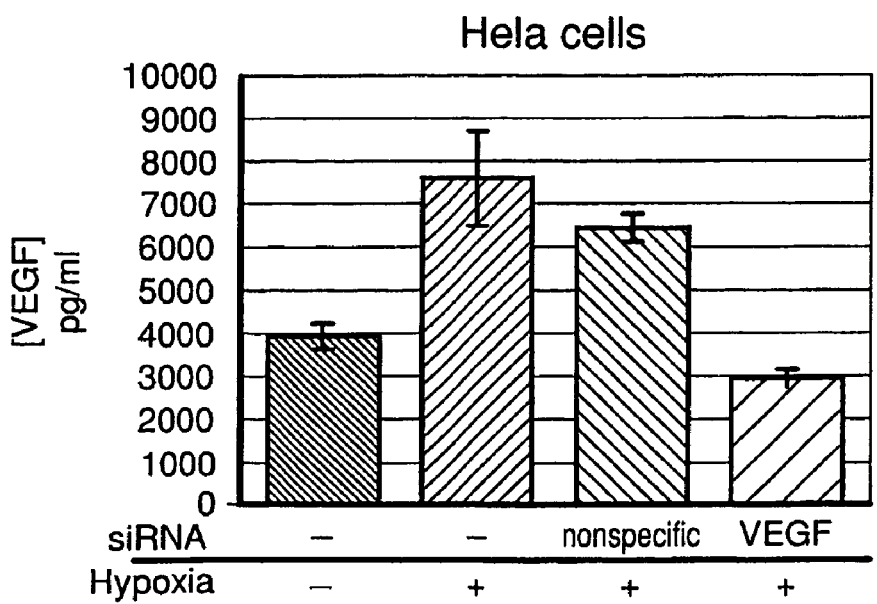

As can be seen in FIG. 1, RNAi degradation induced by Cand5 siRNA significantly reduces the concentration of VEGF produced by the hypoxic 293 and HeLa cells. There was essentially no difference in the amount of VEGF produced by hypoxic cells treated with either no siRNA or the non-specific siRNA control. Similar results were also seen with human ARPE19 cells treated under the same conditions. Thus, RNA interference with VEGF-targeted siRNA disrupts the pathogenic up-regulation of VEGF in human cultured cells in vitro.

The experiment outlined above was repeated on mouse NIH 3T3 cells using a mouse-specific VEGF siRNA (see Example 6 below), and VEGF production was quantified with a mouse VEGF ELISA (R&D systems, Minneapolis, Minn.) as described in the Quantikine mouse VEGF ELISA protocol available from the manufacturer, the entire disclosure of which is herein incorporated by reference. Results similar to those reported in FIG. 1 for the human cell lines were obtained.

EXAMPLE 2

Effect of Increasing siRNA Concentration on VEGF Production in Human Cultured Cells The experiment outlined in Example 1 was repeated with human 293, HeLa and ARPE19 cells using a range of siRNA concentrations from 10 nM to 50 nM. The ability of the Cand5 siRNA to down-regulate VEGF production increased moderately up to approximately 13 nM siRNA, but a plateau effect was seen above this concentration. These results highlight the catalytic nature of siRNA-mediated RNAi degradation of mRNA, as the plateau effect appears to reflect VEGF production from the few cells not transfected with the siRNA. For the majority of cells which had been transfected with the siRNA, the increased VEGF mRNA production induced by the hypoxia is outstripped by the siRNA-induced degradation of the target mRNA at siRNA concentrations greater than about 13 nM.

EXAMPLE 3

Specificity of siRNA Targeting

NIH 3T3 mouse fibroblasts were grown in 24-well plates under standard conditions, so that the cells were ~50% confluent one day prior to transfection. The human VEGF siRNA Cand5 was transfected into a NIH 3T3 mouse fibroblasts as in Example 1. Hypoxia was then induced in the transfected cells, and murine VEGF concentrations were measured by ELISA as in Example 1.

Figure 2:
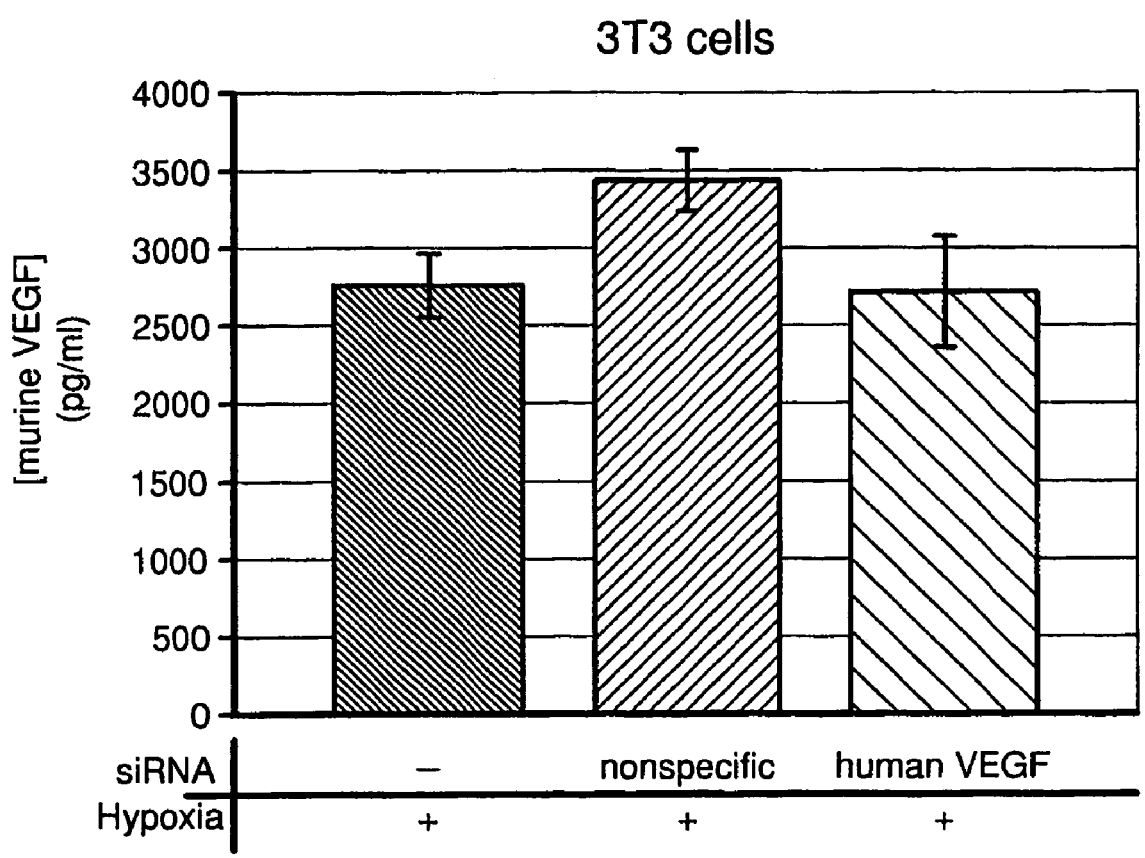
FIG. 2 is a histogram of murine VEGF concentration (in pg/ml) in hypoxic NIH 3T3 cells treated with no siRNA ("-"); nonspecific siRNA ("nonspecific"); or siRNA targeting human VEGF mRNA ("VEGF"). Each bar represents the average of six experiments and the error is the standard deviation of the mean.
Figure 3:
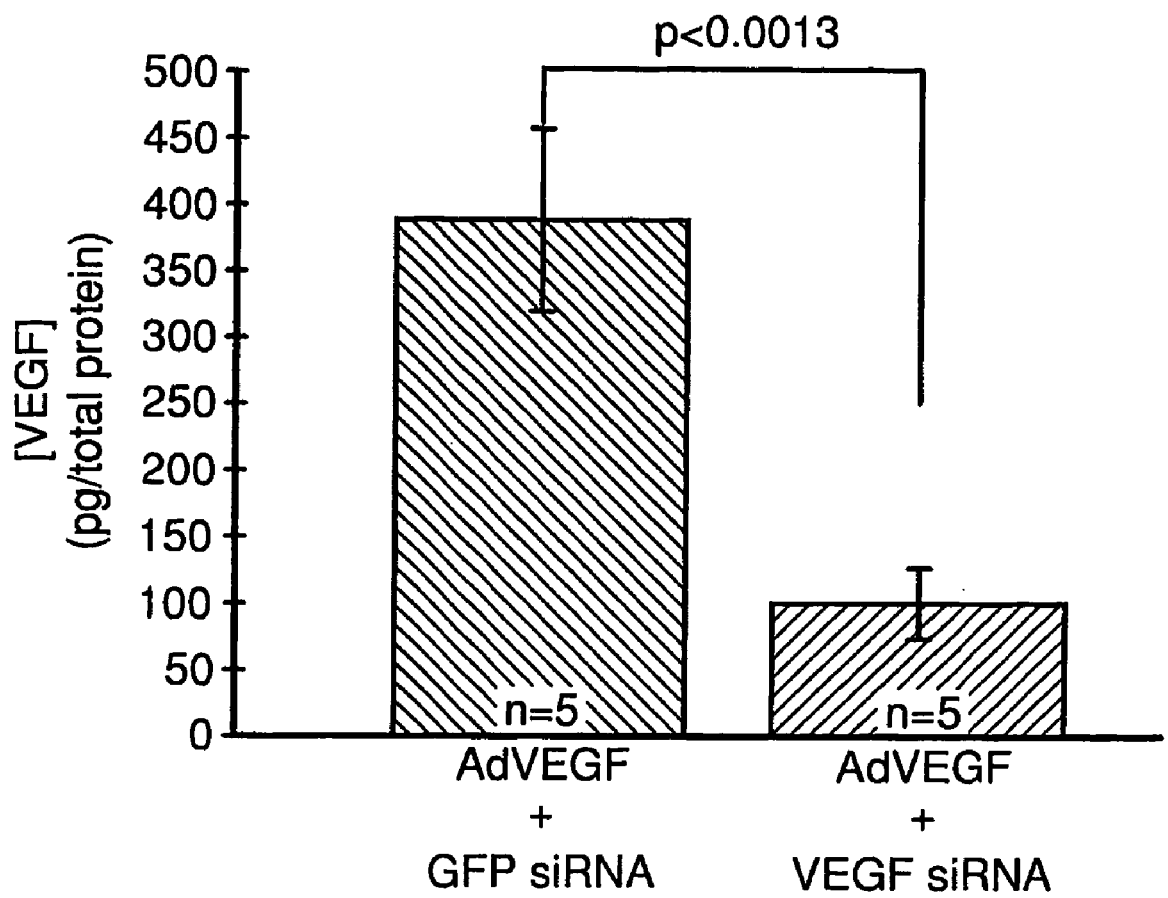
FIG. 3 is a histogram of human VEGF concentration (pg/total protein) in retinas from mice injected with adenovirus expressing human VEGF ("AdVEGF") in the presence of either GFP siRNA (dark gray bar) or human VEGF siRNA (light grey bar). Each bar represents the average of 5 eyes and the error bars represent the standard error of the mean.

The sequence targeted by the human VEGF siRNA Cand5 differs from the murine VEGF mRNA by one nucleotide. As can be seen in FIG. 2, the human VEGF siRNA has no affect on the ability of the mouse cells to up-regulate mouse VEGF after hypoxia. These results show that siRNA induced RNAi degradation is sequence-specific to within a one nucleotide resolution.

EXAMPLE 4

In Vivo delivery of siRNA to Murine Retinal Pigment Epithelial Cells

VEGF is upregulated in the retinal pigment epithelial (RPE) cells of human patients with age-related macular degeneration (ARMD). To show that functional siRNA can be delivered to RPE cells in vivo, GFP was expressed in mouse retinas with a recombinant adenovirus, and GFP expression was silenced with siRNA. The experiment was conducted as follows.

One eye from each of five adult C57/Black6 mice (Jackson Labs, Bar Harbor, Me.) was injected subretinally as described in Bennett et al. (1996), supra., with a mixture containing ~1×10⁸ particles of adenovirus containing eGFP driven by the CMV promoter and 20 picomoles of siRNA targeting eGFP conjugated with transit TKO reagent (Mirus).

As positive control, the contralateral eyes were injected with a mixture containing ~1×10⁸ particles of adenovirus containing eGFP driven by the CMV promoter and 20 picomoles of siRNA targeting human VEGF conjugated with transit TKO reagent (Mirus). Expression of GFP was detected by fundus ophthalmoscopy 48 hours and 60 hours after injection. Animals were sacrificed at either 48 hours or 60 hours post-injection. The eyes were enucleated and fixed in 4% paraformaldehyde, and were prepared either as flat mounts or were processed into 10 micron cryosections for fluorescent microscopy.

No GFP fluorescence was detectable by ophthalmoscopy in the eyes which received the siRNA targeted to GFP mRNA in 4 out of 5 mice, whereas GFP fluorescence was detectable in the contralateral eye which received the non-specific control siRNA. A representative flat mount analyzed by fluorescence microscopy showed a lack of GFP fluorescence in the eye which received GFP siRNA, as compared to an eye that received the non-specific control siRNA. Cryosections of another retina showed that the recombinant adenovirus efficiently targets the RPE cells, and when the adenovirus is accompanied by siRNA targeted to GFP mRNA, expression of the GFP transgene is halted.

While there is some GFP fluorescence detectable by fluorescence microscopy in eyes that received siRNA targeted to GFP mRNA, the fluorescence is greatly suppressed as compared to controls that received non-specific siRNA. These data demonstrate that functional siRNA can be delivered in vivo to RPE cells.

EXAMPLE 5

In Vivo Expression and siRNA-Induced RNAi Degradation of Human VEGF in Murine Retinas In order to demonstrate that siRNA targeted to VEGF functioned in vivo, an exogenous human VEGF expression cassette was delivered to mouse RPE cells via an adenovirus by subretinal injection, as in Example 4. One eye received Cand5 siRNA, and the contralateral eye received siRNA targeted to GFP mRNA. The animals were sacrificed 60 hours post-injection, and the injected eyes were removed and snap frozen in liquid $N_2$ following enucleation. The eyes were then homogenized in lysis buffer, and total protein was measured using a standard Bradford protein assay (Roche, Germany). The samples were normalized for total protein prior to assaying for human VEGF by ELISA as described in Example 1.

Figure 4:
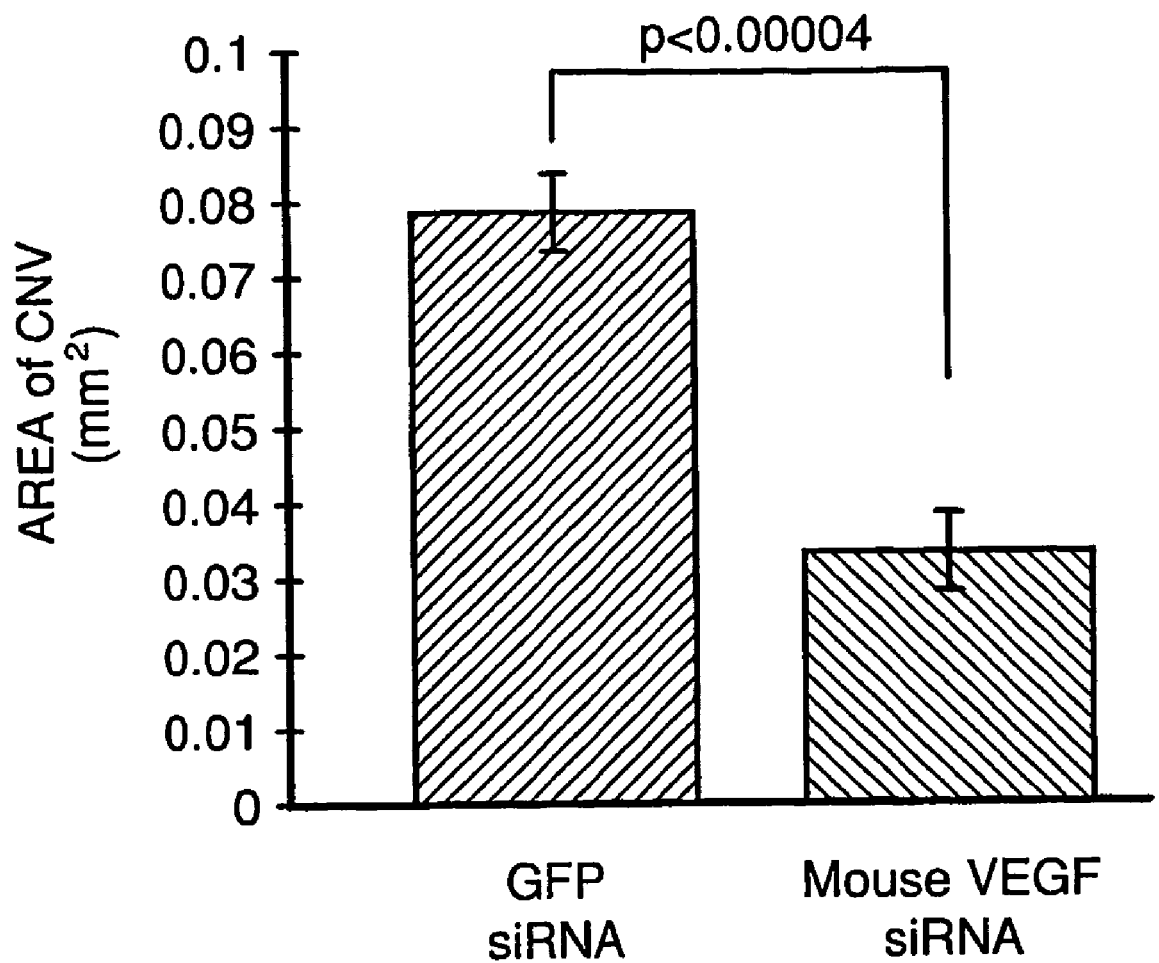
FIG. 4 is a histogram showing the mean area (in mm$^2$) of laser-induced CNV in control eyes given subretinal injections of GFP siRNA (N=9; "GFP siRNA"), and in eyes given subretinal injections of mouse VEGF siRNA (N=7; "Mouse VEGF siRNA"). The error bars represent the standard error of the mean.

The expression of VEGF was somewhat variable from animal to animal. The variability of VEGF levels correlated well to those observed in the GFP experiments of Example 4, and can be attributed to some error from injection to injection, and the differential ability of adenovirus to delivery the target gene in each animal. However, there was a significant attenuation of VEGF expression in each eye that received VEGF siRNA, as compared to the eyes receiving the non-specific control siRNA (FIG. 4). These data indicate that the Cand5 siRNA was potent and effective in silencing human VEGF expression in murine RPE cells in vivo.

EXAMPLE 6

Inhibition of Choroidal Neovascularization in the Mouse CNV Model

There is evidence that choroidal neovascularization in ARMD is due to the upregulation of VEGF in the RPE cells. This human pathologic condition can be modeled in the mouse by using a laser to burn a spot on the retina ("laser photo-coagulation" or "laser induction"). During the healing process, VEGF is believed to be up-regulated in the RPE cells of the burned region, leading to re-vascularization of the choroid. This model is called the mouse choroidal neovascularization ("CNV") model.

For rescue of the mouse CNV model, a mouse siRNA was designed that incorporated a one nucleotide change from the human "Cand5" siRNA from Example 1. The mouse siRNA specifically targeted mouse VEGF mRNA at the sequence AAACCUCACCAAAGCCAGCAC (SEQ ID NO: 80). Other siRNA that target mouse VEGF were also designed and tested. The GFP siRNA used as a nonspecific control in Example 1 was also used as a non-specific control here.

Twenty four hours after laser induction, one eye from each of eleven adult C57/Black6 mice (Jackson Labs, Bar Harbor, Me.) was injected subretinally with a mixture containing ~1×10$^8$ particles of adenovirus containing LacZ driven by the CMV promoter and 20 picomoles of siRNA targeting mouse VEGF conjugated with transit TKO reagent (Mirus), as in Example 4. As a control, contralateral eyes received a mixture containing ~1×10$^8$ particles of adenovirus containing LacZ driven by the CMV promoter and 20 picomoles of siRNA targeting GFP conjugated with transit TKO reagent (Mirus).

Fourteen days after the laser treatment, the mice were perfused with fluorescein and the area of neovascularization was measured around the burn spots. Areas of the burn spots in the contra-lateral eye were used as a control. The site of neovascularization around the burn spots in animals that received siRNA targeting mouse VEGF was, on average, ¼ the area of the control areas. These data support the use of VEGF-directed siRNA (also called "anti-VEGF siRNA") for therapy of ARMD.

EXAMPLE 7

Generation of an Adeno-Associated Viral Vector for Expression of siRNA

A "cis-acting" plasmid for generating a recombinant AAV vector for delivering an siRNA was generated by PCR based subcloning, essentially as described in Samulski R et al. (1987), supra. The cis-acting plasmid was called "pAAV-siRNA."

Figure 5:
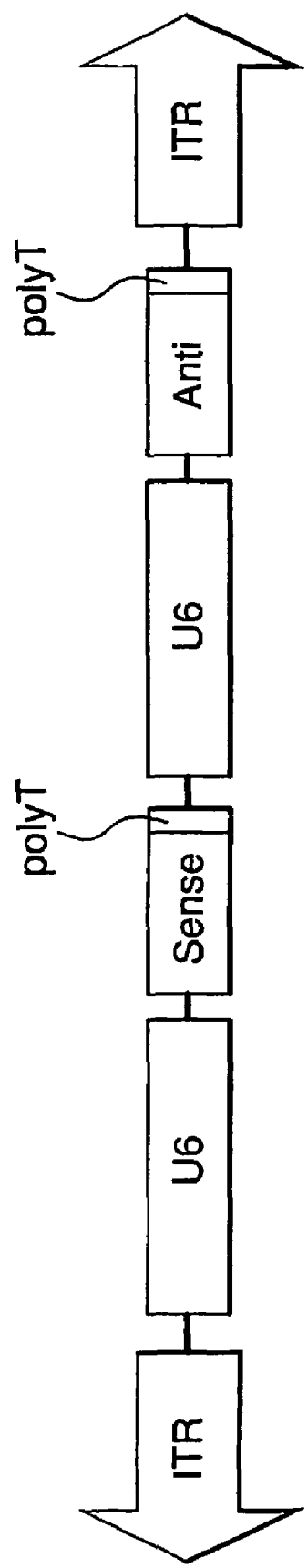
FIG. 5 is a schematic representation of pAAVsiRNA, a cis-acting plasmid used to generate a recombinant AAV viral vector of the invention. "ITR": AAV inverted terminal repeats; "U6": U6 RNA promoters; "Sense": siRNA sense coding sequence; "Anti": siRNA antisense coding sequence; "PolyT": polythymidine termination signals.

The rep and cap genes of psub201 were replaced with the following sequences in this order: a 19 nt sense RNA strand coding sequence in operable connection with a polyT termination sequence under the control of a human U6 RNA promoter, and a 19 nt antisense RNA strand coding sequence in operable connection with a polyT termination sequence under the control of a human U6 RNA promoter. A schematic representation of pAAVsiRNA is given if FIG. 5.

A recombinant AAV siRNA vector was obtained by transfecting pAAVsiRNA into human 293 cells previously infected with E1-deleted adenovirus, as described in Fisher K J et al. (1996), supra. The AAV rep and cap functions were provided by a trans-acting plasmid pAAV/Ad as described in Samulski R et al. (1989), supra. Production lots of the recombinant AAV siRNA vector were titered according to the number of genome copies/ml, as described in Fisher K J et al. (1996), supra.

EXAMPLE 8

VEGF-Directed siRNA Inhibits Experimental Choroidal Neovascularization

The ability of murine VEGF-directed siRNA to inhibit experimental laser-induced choroidal neovascularization (CNV) in mice was tested as follows.

The retinas of adult female C57BL/6 mice were laser photocoagulated using an 810 nm diode laser (75 um, 140 mw, 0.10 seconds) (OcuLight Six; IRIS Medical, Mountain View, Calif.). Three laser spots were applied to both eyes of each mouse. Thirty-six hours following laser photocoagulation, an siRNA targeted to mouse VEGF ("mVEGF1.siRNA") was delivered subretinally or intravitreally to one eye of each mouse. For subretinal injection, the siRNA was conjugated with Transit TKO transfection reagent (Mirus) and mixed with recombinant adenovirus (rAdenovirus). For intravitreal injection, the siRNA was delivered in the absence of transfection reagent and rAdenovirus. As a control, the contralateral eyes of each mouse received subretinal or intravitreal injections of identical formulations with an siRNA targeted to GFP ("GFP1.siRNA"), which has no homology to mouse VEGF.

Figure 6A:
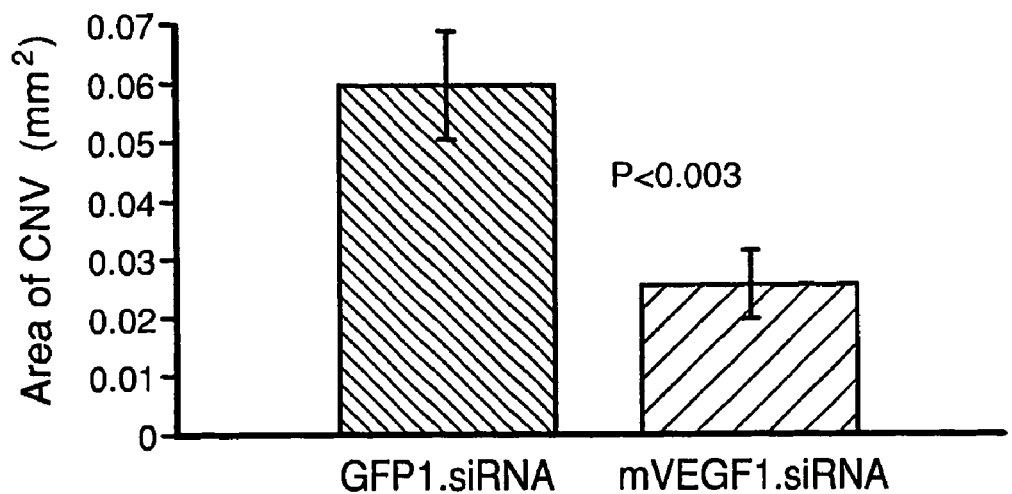
FIG. 6 shows histograms of the mean area (in mm$^2$) of laser-induced CNV in treatment in mouse eyes injected (A) subretinally or (B) intravitreally with a mouse anti-VEGF siRNA ("mVEGF1.siRNA") or control siRNA ("GFP1.siRNA"). The error bars represent the standard error of the mean. (C) is a histogram of the mean area (in mm$^2$) of laser-induced CNV in mouse eyes injected intravitreally with: phosphate-buffered saline with no siRNA at 1 day post-laser induction ("PBS"; CNV area measured at 14 days post-laser induction); control siRNA at 14 days post-laser induction ("GFP1.siRNA"; CNV area measured at 21 days post-laser induction); or a mouse anti-VEGF siRNA at 14 days post-laser induction ("mVEGF1.siRNA"; CNV area measured at 21 days post-laser induction). The error bars represent the standard error of the mean.
Figure 6B:
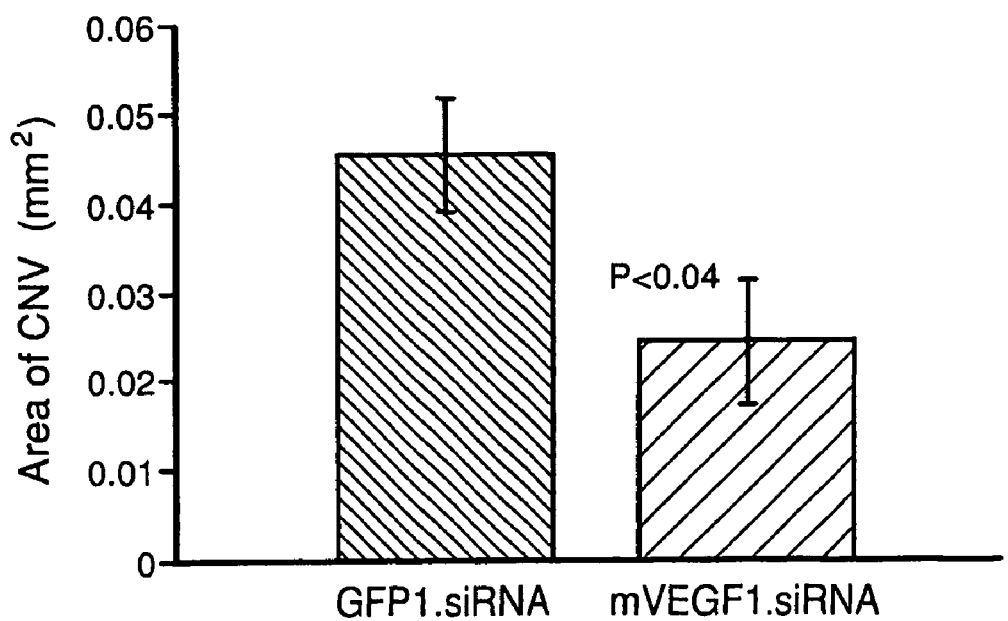

Fourteen days following laser treatment, all animals were perfused with high molecular weight FITC-dextran, choroidal flat mounts were prepared as described above, and the flat mounts were photographed and analyzed microscopically in a masked fashion. The area of CNV in each flat mount was measured with Openlab software (Improvision, Boston, Mass.). The mean areas of CNV in eyes treated with mVEGF1.siRNA were significantly smaller than those areas from GFP1.siRNA-treated eyes for both subretinal (FIG. 6A; P<0.003) and intravitreal (FIG. 6B; P<0.04) delivery.

In a second experiment, the retinas of adult female C57BL/6 mice were laser photocoagulated as described above, and the animals were divided into control and test groups. One day following laser photocoagulation, phosphate buffered saline was delivered intravitreally to the animals of the control group, which were perfused with dextran-fluorescein 14 days after laser treatment. Choroidal flat mounts were then prepared and the areas of CNV in each flat mount were measured as above.

Fourteen days following laser photocoagulation, mVEGF1.siRNA was delivered by intravitreal injection into one eye of each mouse in the test group. Contralateral eyes were injected with GFP1.siRNA as a control. The test group animals were perfused with high molecular weight dextran-fluorescein 21 days after laser treatment. Choroidal flat mounts were then prepared and the areas of CNV in each flat mount were measured, as above.

Figure 6C:
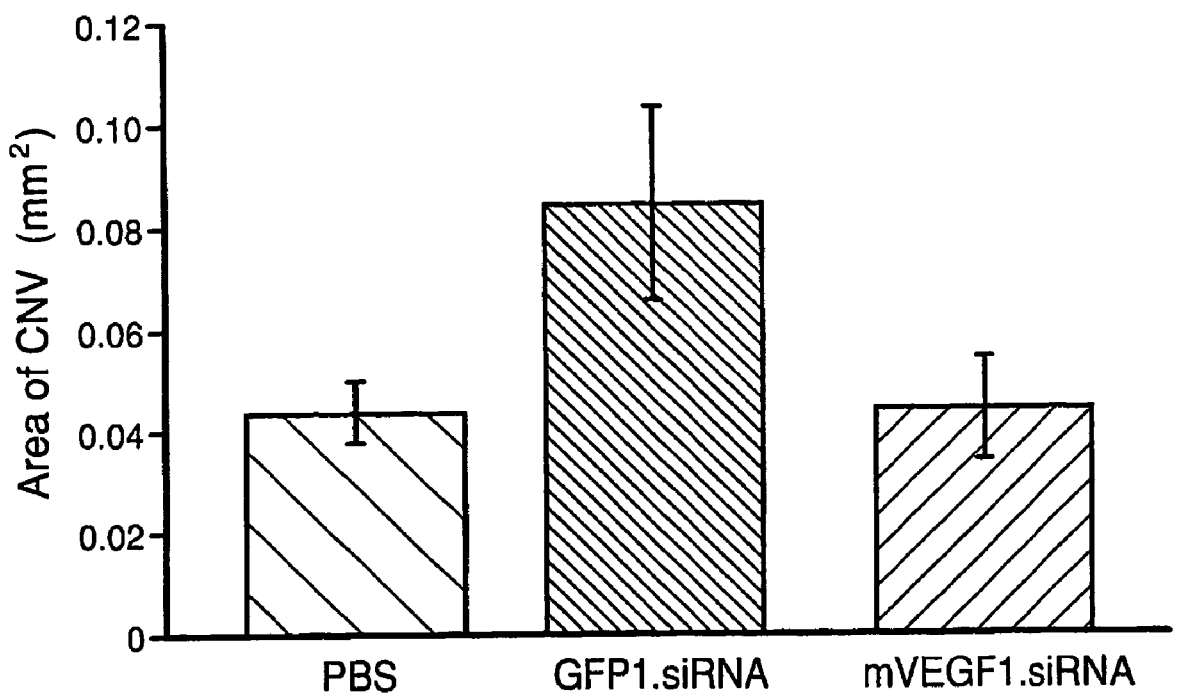

In this latter experiment, the anti-VEGF siRNA was administered during CNV growth, as opposed to before CNV growth, and thus is more representative of the condition of human patients presenting with wet AMD. As can be seen from FIG. 6, the mean areas of CNV in mVEGF1.siRNA-treated eyes were significantly smaller than those areas measured in GFP1.siRNA-treated eyes (FIG. 6C; P<0.05). The mean areas of CNV in mVEGF1.siRNA-treated eyes at day 21 and control ("PBS") eyes at day 14 were not significantly different (FIG. 6C; P=0.469).

The results of these experiments indicate that age-related macular degeneration can be treated with anti-VEGF siRNA.

EXAMPLE 9

In Vivo RNA Interference of Human VEGF Induced by Anti-VEGF siRNA in Murine RPE Cells The ability of Cand5 siRNA to induce RNAi of VEGF in vivo over time was evaluated as follows.

AAV.CMV.VEGF, which expresses human VEGF from an adeno-associated viral vector, was generously provided by Dr. A. Auricchio. AAV.CMV.VEGF was injected subretinally and bilaterally in eyes of five C57B1/6 mice. Twenty-eight days after injection of AAV.CMV.VEGF, Cand5 siRNA was delivered by intravitreal injection into one eye and control GFP1.siRNA was delivered by intravitreal injection in the contralateral eye of each animal.

At day 0 (pre-siRNA injection), and at 6, 10 and 14 days after siRNA injection, the mice were sacrificed and the eyes were snap frozen in liquid nitrogen following enucleation. The eyes were then homogenized in lysis buffer (Roche, Basel, Switzerland), and total protein was measured using a Bradford assay, as in Example 5 above. Two mice were used for the 0 day time point (n=2), and three mice each were used for the 6, 10 and 14 day time points (n=3). The samples were normalized for total protein prior to assaying for human VEGF by ELISA, according to the manufacturer's recommendations (R&D systems, Minneapolis, Minn.). Percent of VEGF (% VEGF) for each mouse was calculated as the concentration of VEGF ("[VEGF]") in the eye injected with Cand5 divided by the [VEGF] in the eye injected with GFP1.siRNA, multiplied by 100.

Figure 7:
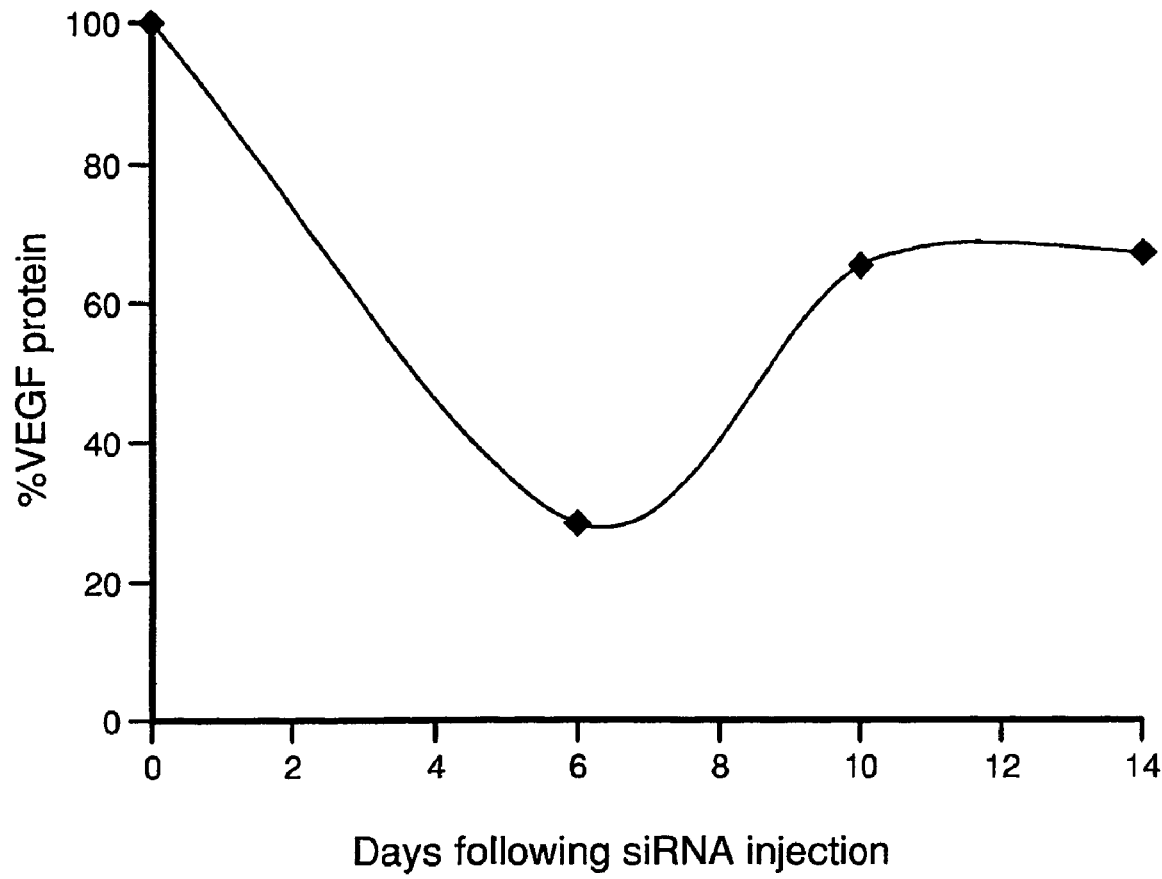
FIG. 7 is a graph of the percent of VEGF ("% VEGF") protein in mouse eyes injected sub-retinally with human anti-VEGF siRNA ("Cand5") and control siRNA ("GFP1.siRNA") at 0 (n=2; pre-siRNA injection), 6 (n=3), 10 (n=3) and 14 (n=3) days post-injection. % VEGF=([VEGF] in the Cand5 eye/[VEGF] in the GFP1.siRNA eye)*100.

As can be seen from FIG. 7, a single injection of Cand5 induced an RNAi-mediated decrease in VEGF levels of approximately 70% by day 6 post-siRNA injection, with a reduction in VEGF production of approximately 35% continuing through at least day 14 post-siRNA injection. These results indicate that siRNA directed against human VEGF is capable of inducing RNAi of human VEGF in vivo for a sustained period of time.

EXAMPLE 10

In Vivo RNA Interference of VEGF in Monkeys with Anti-VEGF siRNA

The objectives of this study were to determine the safety and efficacy of Cand5 when administered by single intravitreal injection to male cynomolgus monkeys following induction of CNV. Cand5 was administered in the vehicle control article to naive male cynomolgus monkeys in the following dose levels: 0 mg/eye (control), 0.07 mg/eye, 0.18 mg/eye, 0.35 mg/eye and, and 0.70 mg/eye.

CNV was induced by laser treatment to the maculae of both eyes of each animal, and the doses of Cand5 were given shortly following laser treatment. The animals were evaluated for changes in clinical signs, body weight and ocular condition (extensive ophthalmic examinations, electroretinography and tonometry). Fluorescein angiography was performed and blood samples were collected. At the end of the study (Day 44), all animals were euthanized and a complete gross necropsy was performed. Selected tissues were collected and preserved for histopathologic evaluation.

No adverse systemic or local (ocular) effects of Cand5 were detected when monkeys were administered a single intravitreal injection into both eyes at doses up to 0.70 mg/eye following laser lesioning of the macula and during subsequent development of CNV.

EXAMPLE 11

In Vitro RNA Interference of VEGF with Anti-VEGF siRNA in Human Embryonic Kidney 293 Cells Human embryonic kidney 293 cells (obtained from ATCC, Manassas, Va.) were cultured in Dulbecco's Modified Eagle Medium (DMEM; obtained from Celigro, Herndon, Va.) with 10% fetal bovine serum (FBS; from JRH Biosciences, Lenexa, Kans.) and an antibiotic-antimycotic reagent, used for the prevention of cell culture growth contaminants (from Gibco, Carlsbad, Calif.).

siRNAs were synthesized by Integrated DNA Technologies (Coralville, Iowa). The siRNA target sequences are shown in Table 2. An additional siRNA was used in this study that targets the gene of enhanced green fluorescent protein (EGFP) as a negative control.

TABLE 2

| Name | GC Content | Nucleotide Start Site | Target Sequence 5'-3' |
|---|---|---|---|
| hVEGF#1 | 58% | 92 | aaggaggagggcagaatcatc (SEQ ID NO: 81) |
| hVEGF#2 | 42% | 124 | aagttcatggatgtctatcag (SEQ ID NO: 47) |

TABLE 2-continued

| Name | GC Content | Nucleotide Start Site | Target Sequence 5'-3' |
|---|---|---|---|
| hVEGF#3 | 58% | 162 | aatcgagaccctggtggacat (SEQ ID NO: 48) |
| hVEGF#4 | 42% | 301 | aacatcaccatgcagattatg (SEQ ID NO: 50) |
| hVEGF#5 | 58% | 338 | aaggccagcacataggagaga (SEQ ID NO: 52) |
| hVEGF#6 | 42% | 380 | aatgtgaatgcagaccaaaga (SEQ ID NO: 82) |
| hVEGF#7 | 37% | 396 | aaagaaagatagagcaagaca (SEQ ID NO: 56) |
| hVEGF#8 | 32% | 450 | aaagcatttgtttgtacaaga (SEQ ID NO: 83) |
| hVEGF#9 | 42% | 467 | aagatccgcagacgtgtaaat (SEQ ID NO: 84) |
| hVEGF#10 | 53% | 498 | aaacacacactcgcgttgcaa (SEQ ID NO: 85) |
| Cand5 | 63% | 328 | aaacctcaccaaggccagcac (SEQ ID NO: 51) | siRNA Transfection and Hypoxia Induction In Vitro. Human 293 cells were cultured in 24 well plates at 37° C. with 5% $CO_2$ overnight. The next day, transfections were performed when cells were about 50%-70% confluent. Cells were transfected with siRNAs directed against human VEGF. siRNAs were mixed in a CaPi reagent and added to 20 µl of 250 mM $CaCl_2$ solution. The siRNA/$CaCl_2$ mixture was added drop-wise to 20 µl of 2× Hanks Balanced Salt Solution (HBS), while mixing by vortex. The siRNA/$CaCl_2$/HBS complex was added directly to the medium in each well (300 µL/well). After a 4-hour incubation at 37° C., the medium was removed, and the cells were further incubated with 10% DMSO-containing serum-free medium (300 µL/well at room temperature for 1-2 minutes). This medium was then removed, and the cells were fed again with growth medium (500 µL/well). Negative controls included transfection reagent lacking siRNA and nonspecific siRNA (eEGFP1 siRNA). For screening experiments siRNAs were used at a concentration of 25 nM. For dose response experiments, siRNAs were used at concentrations of 1 nM, 5 nM and 25 nM. Hypoxia was induced with desferrioxamine at a final concentration of 130 uM 4 hours after transfection was performed. Desferrioxamine mimics a hypoxic state, as it is proposed to disrupt normal oxygen-sensing pathways in mammalian cells by inhibiting heme-Fe2+ interactions.

VEGF Protein Quantification. Approximately 48 hours post transfection, the supernatant was removed from all wells and a human VE GF ELISA (R & D systems, Minneapolis, Minn.) was performed on the 293 cells as described in the Quantikine human VEGF ELISA protocol. VEGF-specific Antibody was added to each well causing color development in proportion to the amount of VEGF bound to the plate. ELISA results were read on an AD340 plate reader at 450 nm (Beckman Coulter).

Figure 8:
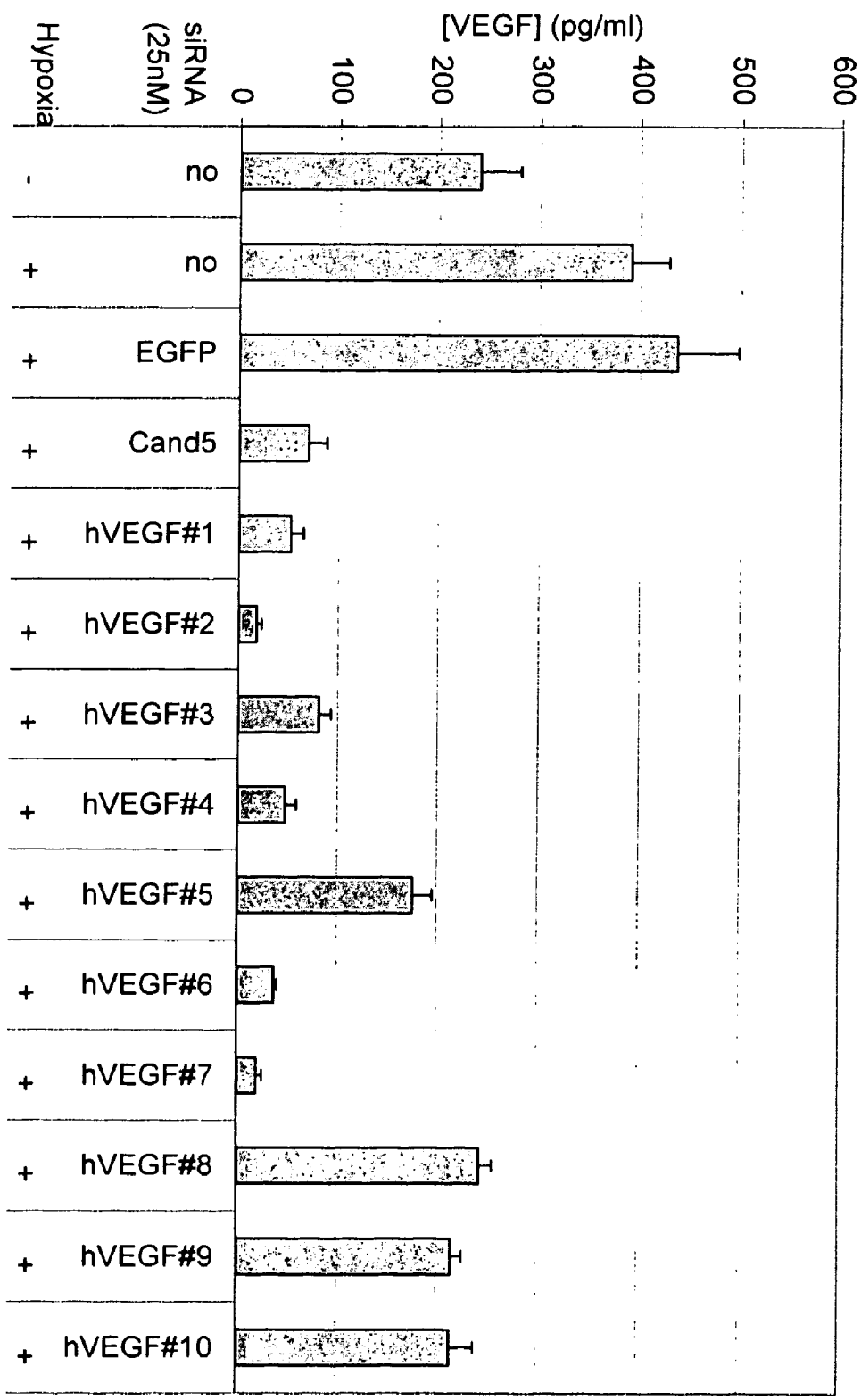
FIG. 8 is a graph of hVEGF protein levels in 293 cells transfected with transfected with human VEGF siRNAs, non-specific siRNA (EGFP siRNA) or mock transfections without siRNA.
Figure 9:
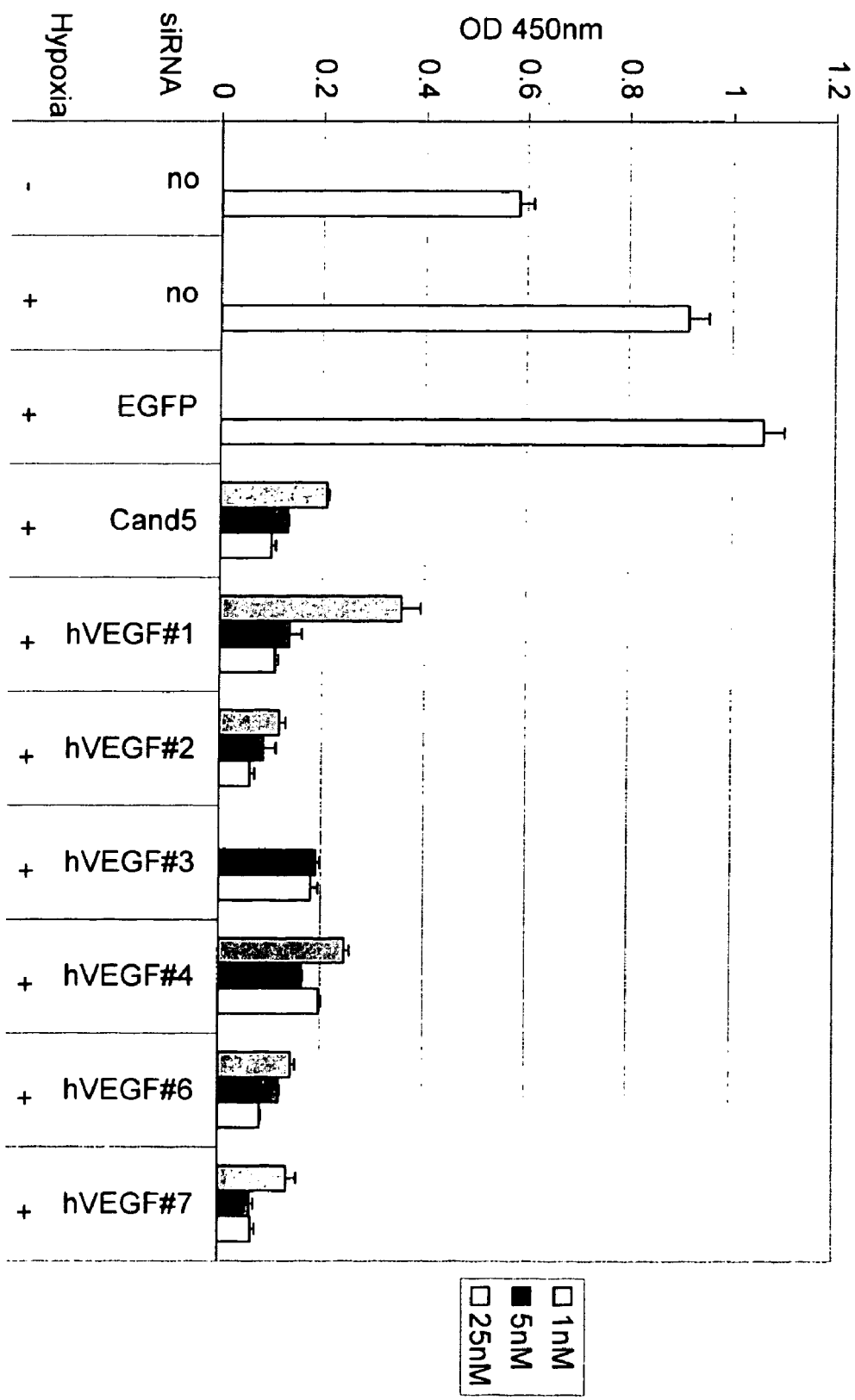
FIG. 9 is a graph of the dose response studies with Cand5, hVEGF#1, hVEGF#2, hVEGF#3, hVEGF#4, hVEGF#6 and hVEGF#7.

Results. Human VEGF siRNAs Suppresses Hypoxia-Induced Up-regulation of Human VEGF Protein in 293 Cells. Human VEGF was upregulated by the desferrioxamine-mediated induction of hypoxia. Readings of OD 450 nm reflected the human VEGF protein levels in cell samples. The hypoxia-induced increase of hVEGF protein levels were significantly reduced in cells transfected with all of the human VEGF siRNAs (FIG. 8). No effect on hVEGF levels were observed with transfections with nonspecific siRNA (EGFP siRNA) or mock transfections without siRNA. Dose response studies were performed on Cand5, hVEGF#1, hVEGF#2, hVEGF#3, hVEGF#4, hVEGF#6 and hVEGF#7 (FIG. 9).

We claim:

1. An isolated siRNA comprising a duplex of a first RNA strand and a second RNA strand, said first RNA strand comprising a nucleotide sequence identical to a target sequence of about 19 to about 25 contiguous nucleotides in human $VEGF_{206}$ mRNA (SEQ ID NO: 5), wherein said target sequence is CGTACTTGCAGATGTGACA (SEQ ID No. 42).

2. The siRNA of claim 1, wherein the first and second RNA strands forming the RNA duplex are covalently linked by a single-stranded hairpin.

3. The siRNA of claim 1, wherein the siRNA further comprises non-nucleotide material.

4. The siRNA of claim 1, wherein the first and second RNA strands are stabilized against nuclease degradation.

5. The siRNA of claim 1, further comprising a 3' overhang.

6. The siRNA of claim 5, wherein the 3' overhang comprises from 1 to about 6 nucleotides.

7. The siRNA of claim 5, wherein the 3' overhang comprises about 2 nucleotides.

8. The siRNA of claim 1, wherein the sense RNA strand comprises a first 3' overhang, and the antisense RNA strand comprises a second 3' overhang.

9. The siRNA of claim 8, wherein the first and second 3' overhangs each comprise from 1 to about 6 nucleotides.

10. The siRNA of claim 8, wherein the first 3' overhang comprises a dinucleotide and the second 3' overhang comprises a dinucleotide.

11. The siRNA of claim 10, where the dinucleotide comprising the first and second 3' overhangs is dithymidylic acid (TT) or diuridylic acid (uu).

12. The siRNA of claim 5, wherein the 3' overhang is stabilized against nuclease degradation.

13. A pharmaceutical composition comprising a siRNA and a pharmaceutically acceptable carrier, said siRNA comprising a duplex of a first RNA strand and a second RNA strand, said first RNA strand comprising a nucleotide sequence identical to a target sequence of about 19 to about 25 contiguous nucleotides in human $VEGF_{206}$ mRNA (SEQ ID NO: 5), wherein said target sequence is CGTACTTGCA-GATGTGACA (SEQ ID No. 42).

14. The pharmaceutical composition of claim 13, wherein the first and second RNA strands are stabilized against nuclease degradation.

15. The pharmaceutical composition of claim 13, further comprising at least one 3' overhang.

16. The pharmaceutical composition of claim 15, wherein the at least one 3' overhang comprises about 2 nucleotides.

17. The pharmaceutical composition of claim 15, where the at least one 3' overhang comprises a dithymidylic acid (TT) or diuridylic acid (uu).

18. The pharmaceutical composition of claim 13, wherein the sense RNA strand comprises a first 3' overhang, and the antisense RNA strand comprises a second 3' overhang.

* * * * *

UNITED STATES PATENT AND TRADEMARK OFFICE
CERTIFICATE OF CORRECTION

PATENT NO. : 7,674,895 B2  Page 1 of 1
APPLICATION NO. : 11/518524
DATED : March 9, 2010
INVENTOR(S) : Reich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 614 days.

Signed and Sealed this

Twenty-sixth Day of October, 2010

David J. Kappos
*Director of the United States Patent and Trademark Office*